(12) United States Patent
Do et al.

(10) Patent No.: US 11,744,612 B2
(45) Date of Patent: Sep. 5, 2023

(54) SYSTEMS AND METHODS FOR TISSUE REMOVAL

(71) Applicant: Applied Medical Resources Corporation, Rancho Santa Margarita, CA (US)

(72) Inventors: Alexandra Do, San Clemente, CA (US); Boun Pravong, Rancho Santa Margarita, CA (US); Serene Wachli, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 707 days.

(21) Appl. No.: 16/773,639

(22) Filed: Jan. 27, 2020

(65) Prior Publication Data
US 2020/0163697 A1 May 28, 2020

Related U.S. Application Data

(63) Continuation of application No. 15/348,089, filed on Nov. 10, 2016, now Pat. No. 10,568,659, which is a
(Continued)

(51) Int. Cl.
*A61B 17/34* (2006.01)
*B29C 67/00* (2017.01)
(Continued)

(52) U.S. Cl.
CPC ...... *A61B 17/3423* (2013.01); *A61B 17/0293* (2013.01); *B29C 51/004* (2013.01);
(Continued)

(58) Field of Classification Search
CPC ..... B29C 33/485; B29C 51/004; B29C 57/02; B29C 67/0022; A61B 2017/00526;
(Continued)

(56) References Cited

U.S. PATENT DOCUMENTS 1,550,403 A 8/1925 Turkus
2,013,892 A 9/1935 Lucas
(Continued)

FOREIGN PATENT DOCUMENTS

DE 4405831 A1 8/1995
DE 102013217513 A1 3/2015
(Continued)

OTHER PUBLICATIONS

European Patent Office, Extended European Search Report for European Patent Application No. EP 2 0165706.1, titled "Systems and Methods for Tissue Removal," dated Jul. 9, 2020, 8 pgs.
(Continued)

*Primary Examiner* — Matthew P Travers
(74) *Attorney, Agent, or Firm* — Shirin Bozorgui; Patrick Ikehara

(57) ABSTRACT

A guard for providing a cut-resistant pathway through a body orifice or incision to circumferentially protect tissue at the margin is provided. The guard is made of flexible, cut-resistant mesh material having a plurality of interwoven thermosetting filaments. The guard has a central lumen and at least one flared end. The flared end, which serves to anchor the guard in the body opening, is deformable into a reduced configuration to facilitate its insertion and removal. The layer of mesh stretches laterally to increase the diameter of the central lumen. The flexibility and expandability of the guard allows the guard to conform to body openings of different sizes. The guard may include a drawstring to cinch the flared distal end from the proximal end. The guard is thermoset with the flared distal end that is biased to spring back to its normal, undeformed configuration when released from a deformed configuration.

16 Claims, 19 Drawing Sheets

Related U.S. Application Data continuation of application No. PCT/US2016/029154, filed on Apr. 25, 2016.

(60) Provisional application No. 62/151,736, filed on Apr. 23, 2015.

(51) Int. Cl.

| | | |
|---|---|---|
| *B29C 51/00* | (2006.01) | |
| *A61B 17/02* | (2006.01) | |
| *A61B 90/00* | (2016.01) | |
| *A61B 17/3211* | (2006.01) | |
| *A61B 17/00* | (2006.01) | |
| *B29C 57/02* | (2006.01) | |
| *B29C 33/48* | (2006.01) | |

(52) U.S. Cl.
CPC ....... *B29C 67/0022* (2013.01); *A61B 17/3211* (2013.01); *A61B 17/3431* (2013.01); *A61B 17/3439* (2013.01); *A61B 2017/00287* (2013.01); *A61B 2017/00526* (2013.01); *A61B 2017/0225* (2013.01); *A61B 2017/3429* (2013.01); *A61B 2090/08021* (2016.02); *B29C 33/485* (2013.01); *B29C 57/02* (2013.01)

(58) Field of Classification Search
CPC ........ A61B 2017/0225; A61B 17/0293; A61B 17/3423; A61B 2017/3429; A61B 17/3431; A61B 17/3439; A61B 2090/08021

See application file for complete search history.

(56) References Cited

U.S. PATENT DOCUMENTS

| | | |
|---|---|---|
| 2,812,758 A | 11/1957 | Blumenschein |
| 3,244,169 A | 4/1966 | Baxter |
| 3,762,417 A | 10/1973 | Textor |
| 3,807,393 A | 4/1974 | McDonald |
| 4,120,301 A | 10/1978 | Lovick |
| 4,411,655 A | 10/1983 | Schreck |
| 4,553,537 A | 11/1985 | Rosenberg |
| 4,573,452 A | 3/1986 | Greenberg |
| 5,037,379 A | 8/1991 | Clayman et al. |
| 5,143,082 A | 9/1992 | Kindberg et al. |
| 5,176,659 A | 1/1993 | Mancini |
| 5,213,114 A | 5/1993 | Bailey, Jr. |
| 5,215,521 A | 5/1993 | Cochran et al. |
| 5,215,101 A | 6/1993 | Jacobs et al. |
| 5,224,930 A | 7/1993 | Spaeth et al. |
| 5,231,974 A | 8/1993 | Giglio et al. |
| 5,308,327 A | 5/1994 | Heaven et al. |
| 5,312,416 A | 5/1994 | Spaeth et al. |
| 5,320,627 A | 6/1994 | Sorensen et al. |
| 5,330,483 A | 7/1994 | Heaven et al. |
| 5,337,754 A | 8/1994 | Heaven et al. |
| 5,354,303 A | 10/1994 | Spaeth et al. |
| 5,368,545 A | 11/1994 | Schaller et al. |
| 5,413,338 A * | 5/1995 | Kawamatsu .......... B29C 53/824 473/319 |
| 5,465,731 A | 11/1995 | Bell et al. |
| 5,486,183 A | 1/1996 | Middleman et al. |
| 5,520,610 A | 5/1996 | Giglio et al. |
| 5,611,803 A | 3/1997 | Heaven et al. |
| 5,618,296 A | 4/1997 | Sorensen et al. |
| 5,636,639 A | 6/1997 | Turturro et al. |
| 5,647,372 A | 7/1997 | Tovey et al. |
| 5,649,550 A | 7/1997 | Crook |
| 5,669,927 A | 9/1997 | Boebel et al. |
| 5,769,794 A | 6/1998 | Conlan et al. |
| 5,785,677 A | 7/1998 | Auweiler |
| 5,788,709 A | 8/1998 | Riek et al. |
| 5,796,045 A * | 8/1998 | Lancien .................. B29C 57/02 174/136 |
| 5,810,721 A | 9/1998 | Mueller et al. |
| 5,836,936 A | 11/1998 | Cuschieri |
| 5,895,392 A | 4/1999 | Riek et al. |
| 5,957,884 A | 9/1999 | Hooven |
| 5,971,995 A | 10/1999 | Rousseau |
| 6,036,681 A | 3/2000 | Hooven |
| 6,039,748 A | 3/2000 | Savage et al. |
| 6,045,566 A | 4/2000 | Pagedas |
| 6,048,309 A | 4/2000 | Flom et al. |
| 6,059,793 A | 5/2000 | Pagedas |
| 6,142,935 A | 11/2000 | Flom et al. |
| 6,162,172 A | 12/2000 | Cosgrove et al. |
| 6,183,503 B1 * | 2/2001 | Hart ...................... A61F 2/86 623/1.1 |
| 6,206,889 B1 | 3/2001 | Bernardo |
| 6,228,095 B1 | 5/2001 | Dennis |
| 6,254,534 B1 | 7/2001 | Butler et al. |
| 6,258,102 B1 | 7/2001 | Pagedas |
| 6,270,505 B1 | 8/2001 | Yoshida et al. |
| 6,350,267 B1 | 2/2002 | Stefanchik |
| 6,382,211 B1 | 5/2002 | Crook |
| 6,387,102 B2 | 5/2002 | Pagedas |
| 6,406,440 B1 | 6/2002 | Stefanchik |
| 6,569,105 B1 | 5/2003 | Kortenbach et al. |
| 6,685,628 B2 | 2/2004 | Vu |
| 6,814,700 B1 | 11/2004 | Mueller et al. |
| 6,958,037 B2 | 10/2005 | Ewers et al. |
| 7,041,055 B2 | 5/2006 | Young et al. |
| 7,238,154 B2 | 7/2007 | Ewers et al. |
| 7,297,106 B2 | 11/2007 | Yamada et al. |
| 7,377,898 B2 | 5/2008 | Ewers et al. |
| 7,491,168 B2 | 2/2009 | Raymond et al. |
| 7,537,564 B2 | 5/2009 | Bonadio et al. |
| 7,547,310 B2 | 6/2009 | Whitfield |
| 7,670,346 B2 | 3/2010 | Whitfield |
| 7,758,500 B2 | 7/2010 | Boyd et al. |
| 7,758,501 B2 | 7/2010 | Frasier et al. |
| 7,762,969 B2 | 7/2010 | Bilsbury |
| 7,896,877 B2 | 3/2011 | Hall et al. |
| 7,955,292 B2 | 6/2011 | Leroy et al. |
| 7,981,130 B2 | 7/2011 | Seeh |
| 7,998,068 B2 | 8/2011 | Bonadio et al. |
| 8,016,771 B2 | 9/2011 | Orban, III |
| 8,016,839 B2 | 9/2011 | Wilk |
| 8,038,611 B2 | 10/2011 | Raymond et al. |
| 8,075,567 B2 | 12/2011 | Taylor et al. |
| 8,100,928 B2 | 1/2012 | Nohilly et al. |
| 8,114,119 B2 | 2/2012 | Spivey et al. |
| 8,152,820 B2 | 4/2012 | Mohamed et al. |
| 8,157,834 B2 | 4/2012 | Conlon |
| 8,337,510 B2 | 12/2012 | Rieber et al. |
| 8,366,754 B2 | 2/2013 | Teague et al. |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,425,533 B2 | 4/2013 | Parihar et al. |
| 8,517,935 B2 | 8/2013 | Marchek et al. |
| 8,579,914 B2 | 11/2013 | Menn et al. |
| 8,597,180 B2 | 12/2013 | Copeland et al. |
| 8,622,897 B2 | 1/2014 | Raymond et al. |
| 8,721,538 B2 | 5/2014 | Bucholz |
| 8,721,658 B2 | 5/2014 | Kahle et al. |
| 8,734,336 B2 | 5/2014 | Bonadio et al. |
| 8,777,849 B2 | 7/2014 | Haig et al. |
| 8,821,377 B2 | 9/2014 | Collins |
| 8,857,440 B2 | 10/2014 | Gundlapalli et al. |
| 8,864,658 B2 | 10/2014 | Wilkins et al. |
| 8,920,431 B2 | 12/2014 | Shibley et al. |
| 8,956,286 B2 | 2/2015 | Shibley et al. |
| 8,961,408 B2 | 2/2015 | Wilkins et al. |
| 8,961,409 B2 | 2/2015 | O'Prey et al. |
| 9,039,610 B2 | 5/2015 | Wilkins et al. |
| 9,044,210 B1 | 6/2015 | Hoyte et al. |
| 9,168,031 B2 | 10/2015 | Copeland et al. |
| 2003/0078478 A1 | 4/2003 | Bonadio et al. |
| 2003/0216770 A1 * | 11/2003 | Persidsky .......... A61B 17/3439 606/198 |
| 2004/0097960 A1 | 5/2004 | Terachi et al. |
| 2004/0158261 A1 | 8/2004 | Vu |

(56) References Cited

U.S. PATENT DOCUMENTS

| | | |
|---|---|---|
| 2005/0171405 A1 | 8/2005 | Rowland et al. |
| 2005/0197537 A1 | 9/2005 | Bonadio et al. |
| 2005/0253448 A1* | 11/2005 | Meggiolan ............ B60B 27/023 |
| | | 301/105.1 |
| 2005/0267492 A1 | 12/2005 | Poncet et al. |
| 2006/0194027 A1* | 8/2006 | Pourdeyhimi ........ B29C 51/004 |
| | | 428/394 |
| 2006/0200169 A1 | 9/2006 | Sniffin |
| 2006/0200170 A1 | 9/2006 | Aranyi |
| 2006/0247498 A1 | 11/2006 | Bonadio et al. |
| 2007/0051375 A1 | 3/2007 | Milliman |
| 2007/0135780 A1 | 6/2007 | Pagedas |
| 2007/0161866 A1 | 7/2007 | Fowler, Jr. et al. |
| 2007/0161867 A1 | 7/2007 | Fowler, Jr. et al. |
| 2009/0138024 A1 | 5/2009 | Ichihara et al. |
| 2009/0264710 A1 | 10/2009 | Chana et al. |
| 2010/0219091 A1 | 9/2010 | Turner |
| 2011/0054260 A1 | 3/2011 | Albrecht et al. |
| 2011/0184311 A1 | 7/2011 | Parihar et al. |
| 2011/0184435 A1 | 7/2011 | Parihar et al. |
| 2011/0190779 A1 | 8/2011 | Gell et al. |
| 2011/0319719 A1 | 12/2011 | O'Prey et al. |
| 2012/0078264 A1 | 3/2012 | Taylor et al. |
| 2012/0083795 A1 | 4/2012 | Fleming et al. |
| 2012/0109144 A1 | 5/2012 | Chin et al. |
| 2012/0157777 A1 | 6/2012 | Okoniewski |
| 2012/0238823 A1 | 9/2012 | Hagerty et al. |
| 2012/0316572 A1 | 12/2012 | Rosenblatt et al. |
| 2013/0103042 A1 | 4/2013 | Davis |
| 2013/0103043 A1 | 4/2013 | Cabrera |
| 2013/0131457 A1 | 5/2013 | Seckin |
| 2013/0138115 A1 | 5/2013 | Seckin |
| 2013/0184536 A1 | 7/2013 | Shibley et al. |
| 2013/0253267 A1 | 9/2013 | Collins |
| 2013/0284186 A1 | 10/2013 | Touati |
| 2014/0052018 A1 | 2/2014 | Hawkins |
| 2014/0058210 A1 | 2/2014 | Raymond et al. |
| 2014/0058403 A1 | 2/2014 | Menn et al. |
| 2014/0135788 A1 | 5/2014 | Collins |
| 2014/0235952 A1 | 8/2014 | Haig et al. |
| 2014/0236110 A1 | 8/2014 | Taylor et al. |
| 2014/0296649 A1 | 10/2014 | Fehling et al. |
| 2014/0316210 A1 | 10/2014 | Koehler et al. |
| 2014/0330285 A1 | 11/2014 | Rosenblatt et al. |
| 2015/0005584 A1 | 1/2015 | Wilkins et al. |
| 2015/0018625 A1 | 1/2015 | Miraki et al. |
| 2015/0094541 A1 | 4/2015 | Wilkins et al. |
| 2015/0119647 A1 | 4/2015 | Vaillancourt et al. |

FOREIGN PATENT DOCUMENTS

| | | |
|---|---|---|
| EP | 1 312318 A1 | 5/2003 |
| EP | 1 935 356 A1 | 10/2004 |
| EP | 2 138 113 A2 | 12/2009 |
| EP | 2 359 758 A2 | 8/2011 |
| EP | 2 668 907 A2 | 12/2013 |
| WO | WO 00/32116 A1 | 6/2000 |
| WO | WO 00/47117 A1 | 8/2000 |
| WO | WO 03/061480 A1 | 7/2003 |
| WO | WO 03/071926 A2 | 9/2003 |
| WO | WO 2004/075730 A2 | 9/2004 |
| WO | WO 2008/083222 A2 | 7/2008 |
| WO | WO 2011/143410 A1 | 11/2011 |
| WO | WO 2013/093030 A2 | 6/2013 |
| WO | WO 2013/150391 A1 | 10/2013 |
| WO | WO 2015/164591 A1 | 10/2015 |

OTHER PUBLICATIONS

European Patent Office, The International Search Report and Written Opinion for International Application No. PCT/US2015/045705, entitled "Systems and Methods for Tissue Containment and Retrieval," dated Apr. 18, 2016, 18 pgs.

European Patent Office, The International Search Report and Written Opinion for International Application No. PCT/US2015/056978, entitled "Systems and Methods for Tissue Removal," dated Jan. 15, 2016.

European Patent Office, The International Search Report and Written Opinion for International Application No. PCT/US2015/027274, entitled "Suture Clinch with Traction Enhanced," dated Jul. 10, 2015.

European Patent Office, The International Search Report and Written Opinion for International Application No. PCT/US2016/029154, entitled "Systems and Methods for Tissue Removal," dated Aug. 19, 2016, 17 pgs.

The International Bureau of WIPO, International Preliminary Report on Patentability for International Application No. PCT/US2015/027274, entitled "Systems and Methods for Tissue Removal," dated Nov. 3, 2016, 9 pgs.

The International Bureau of WIPO, International Preliminary Report on Patentability for International Application No. PCT/US2015/045705, entitled "Systems and Methods for Tissue Containment and Retrieval," dated Mar. 2, 2017, 10 pgs.

European Patent Office, Invitation to Pay Additional Fees for International Application No. PCT/US2017/014402, titled "Systems and Methods for Tissue Removal", dated Apr. 6, 2017, 10 pgs.

The International Bureau of WIPO, International Preliminary Report on Patentability for International Application No. PCT/US2015/056978, entitled "Systems and Methods for Tissue Removal," dated May 26, 2017, 10 pgs.

European Patent Office, The International Search Report and Written Opinion for International Application No. PCT/US2017/014402, entitled "Systems and Methods for Tissue Removal," dated Jun. 6, 2017, 20 pgs.

The International Bureau of WIPO, International Preliminary Report on Patentability for International Application No. PCT/US2016/029154, entitled "Systems and Methods for Tissue Removal," dated Nov. 2, 2017, 11pgs.

The International Bureau of WIPO, International Preliminary Report on Patentability for International Application No. PCT/US2017/014402, entitled "Systems and Methods for Tissue Removal," dated Aug. 2, 2018, 11pgs.

European Patent Office, Extended European Search Report for European Patent Application No. EP 21163226.0, titled "Systems and Methods for Tissue Removal," dated Jul. 8, 2021, 9 pgs.

European Patent Office, Extended European Search Report for European Patent Application No. EP 21178022.6, titled "Systems and Methods for Tissue Removal," dated Sep. 16, 2021, 8 pgs.

\* cited by examiner

SYSTEMS AND METHODS FOR TISSUE REMOVAL

CROSS-REFERENCE TO RELATED APPLICATIONS

This application is a continuation of U.S. patent application Ser. No. 15/348,089 filed on Nov. 10, 2016 entitled "Systems and methods for tissue removal which is a continuation of International Patent Application No. PCT/US2016/29154 filed on Apr. 25, 2016 entitled "Systems and methods for tissue removal" which claims priority to and benefit of U.S. Provisional Patent Application No. 62/151,736 entitled "Systems and methods for tissue removal" filed on Apr. 23, 2015 all of which are incorporated herein by reference in their entirety.

FIELD OF THE INVENTION

This invention relates to medical devices, and in particular, to systems and methods for the removal of tissue through a body opening.

BACKGROUND OF THE INVENTION

Systems and methods for the surgical removal of tissue through body openings such as small incision sites and/or body orifices are described. Where needed, a small incision is made in a patient to access surgically targeted tissue located inside a body cavity. Surgically targeted tissue may also be approached through a body orifice without an initial incision. Sometimes the targeted tissue is approached directly through the incision or body orifice. Other times, an access device system is placed and/or positioned into, across, at, and/or within the incision and/or body orifice to retract tissue, enlarge, reshape, and/or isolate the incision or body orifice. The access device system serves as a portal for accessing targeted tissue that is located in or adjacent to the body cavity or body orifice. The targeted tissue is detached from adjacent and surrounding tissue employing known surgical techniques and procedures. Once freed, the targeted tissue is ready for removal through the small incision or body orifice. If the targeted tissue is too large to be removed in whole, then it is reduced in size and removed in parts through the small incision. Ideally, the surgeon will "core" or "peel" the targeted tissue to keep it in one piece as much as possible. However, more likely than not, the targeted tissue will be reduced into multiple pieces.

Reducing the size of the targeted tissue is called morcellation. A morcellation procedure includes cutting the targeted tissue into smaller pieces manually with a scalpel or knife, for example, or employing a power morcellator to cut the targeted tissue so that it is removable through the small incision. Pieces of the targeted tissue are removed from the patient through the small incision. As the targeted tissue is being reduced in size in order to fit through the small incision, small pieces of tissue may be cut off and left behind in the patient. As such, morcellation is contraindicated in cases of malignancy or endometriosis. If cancer is morcellated, it can spread malignant tissue and upstage cancer and increase patient mortality.

A hysterectomy is an example of a surgical procedure that may involve morcellation. More than 500,000 hysterectomies are performed annually on women in the United States. Common reasons that a woman may have a hysterectomy are the presence of fibroids, cancer, endometriosis or prolapse. Of these hysterectomies, about 200,000 are performed laparoscopically. When the uterus is too large (>300 g) to be removed through the vagina or if the cervix is still in place, the specimen must be reduced in size to be removed through an abdominal incision or through the vagina. During myomectomy (fibroid removal), large fibroids may also need to be extracted using a morcellation procedure. During morcellation, the targeted tissue (usually a uterus and sometimes adnexal structures) is brought to the abdominal wall surface such as with a tissue grasper and is reduced in size using a blade and removed through the incision from the pelvic cavity. In another variation, the targeted tissue is removed through a body orifice such as through the vagina. Fibroids, or uterine leiomyoma, account for about 30-40% of hysterectomies. These are benign tumors of the uterus that can lead to heavy and painful bleeding. In the past there has been a mild concern that these tumors could be undetected cancer, or Leiomyosarcoma, and it was believed to affect about 1 in 10,000 women. More recent data has come out to support a much higher risk of undetected malignancy in these tumors, putting the range at 1:1000 to 1:400. Because of this elevated risk, many surgeons have begun changing their technique to try to enclose the specimen to do a closed morcellation process by morcellating in a bag to contain errant pieces and prevent dispersion and seeding of tumor cells, rather than morcellating without a bag in a process called open morcellation. Many GYN societies, including AAGL, ACOG, and SGO, have released statements warning of the potential danger of open morcellation. On Apr. 17, 2014, the FDA issued a statement discouraging the use of open power morcellation for hysterectomies and myomectomies for women undergoing these procedures for fibroids. The FDA also increased their estimated of malignant likelihood to 1 in 350. For these reasons, systems and methods are needed to safely and effectively reduce tissue specimens. The present invention sets forth such safe systems and methods for both manual morcellation and power morcellation performed in closed system.

SUMMARY OF THE INVENTION

According to one aspect of the invention, a guard for providing a cut-resistant pathway through a body opening to protect a tissue margin is provided. The guard includes a sidewall having a tubular shape defining a central lumen. The central lumen extends along a longitudinal axis between a proximal opening at a proximal end and a distal opening at a distal end. The sidewall is made of at least one layer of flexible, cut-resistant mesh material having a plurality of interwoven filaments defining interstices. The sidewall has a generally hourglass shape when in a normal, undeformed configuration with a progressively increasing central lumen toward the proximal end defining a proximal flange in the sidewall and a progressively increasing central lumen toward the distal end defining a distal flange in the sidewall. The proximal flange is configured to anchor the guard with respect to a proximal end of the tissue margin and the distal flange is configured to anchor the guard with respect to a distal end of the tissue margin. The sidewall circumferentially protects the tissue margin along the body opening. The sidewall has a neck portion located between the proximal flange and the distal flange. The sidewall is deformable from the normal, undeformed configuration and biased to return to the normal, undeformed configuration when released.

According to another aspect of the invention, a guard for providing a cut-resistant pathway through a body opening defining a tissue margin is provided. The guard includes a sidewall having a tubular shape defining a central lumen extending along a longitudinal axis between a first end and a second end. The sidewall is made of cut-resistant mesh material having a plurality of interwoven filaments defining interstices in a tubular first layer of mesh material. The sidewall is folded to create a fold at a distal end of the guard with the first end and the second end of the sidewall being adjacent to each other at a proximal end of the guard. The folded sidewall forming a tubular second layer of mesh material substantially coaxial with the tubular first layer of mesh material.

According to another aspect of the invention, a guard for protecting a tissue margin along a body opening is provided. The guard includes a tube of cut-resistant mesh material having a plurality of woven polymer filaments. The tube has a first end and a second end and defining a central lumen along a longitudinal axis. The tube has a normal, undeformed shape having at least one flange formed at one of the first end and the second end. The at least one flange extending circumferentially outwardly from the longitudinal axis defining a progressively increasing diameter. The tube includes a neck portion located between the proximal end and the distal end. The neck portion has a diameter that is smaller than the diameter of the at least one flange. The at least one flange is configured to fold distally to a reduced configuration in which the flange has smaller lateral dimension relative to the normal, undeformed shape.

According to another aspect of the invention, a guard for providing a cut-resistant pathway through a body opening to protect a tissue margin is provided. The guard includes a sidewall having a tubular shape defining a central lumen. The central lumen extends along a longitudinal axis between a proximal opening at a proximal end and a distal opening at a distal end. The sidewall is made of at least one layer of flexible, cut-resistant mesh material having a plurality of interwoven filaments defining interstices. The sidewall has a distal portion with a progressively increasing diameter toward the distal end defining a flared distal flange in the sidewall. The distal flange is configured to anchor the guard with respect to a distal end of the tissue margin. The sidewall circumferentially protects the tissue margin along the body opening. The sidewall has a neck portion located proximally to the distal flange. The guard includes a pull-wire located circumferentially around the distal flange and configured to reduce a lateral dimension of the distal flange when pulled into a reduced configuration to facilitate insertion and removal of the guard when in the reduced configuration.

According to another aspect of the invention, a method for manufacturing a tissue guard is provided. The method includes the step of providing a tube of flexible mesh material having a plurality of interwoven filaments defining interstices. The tube is substantially cylindrical in shape having a central lumen extending along the longitudinal axis between a proximal opening at a proximal end and a distal opening at a distal end. A mandrel is provided having at least one outwardly flared flange. The mesh tube is mounted onto the mandrel such that the mandrel is located inside the central lumen and the tube encompasses the mandrel. The mesh tube is heated while the mesh tube is located on the mandrel. The filaments are plastically deformed when heated so that the mesh tube substantially conforms to the shape of the mandrel when the mesh tube is removed from the mandrel. The mesh tube is removed from the mandrel.

DETAILED DESCRIPTION OF THE INVENTION

The following description is provided to enable any person skilled in the art to make and use the surgical tools and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Figure 1:
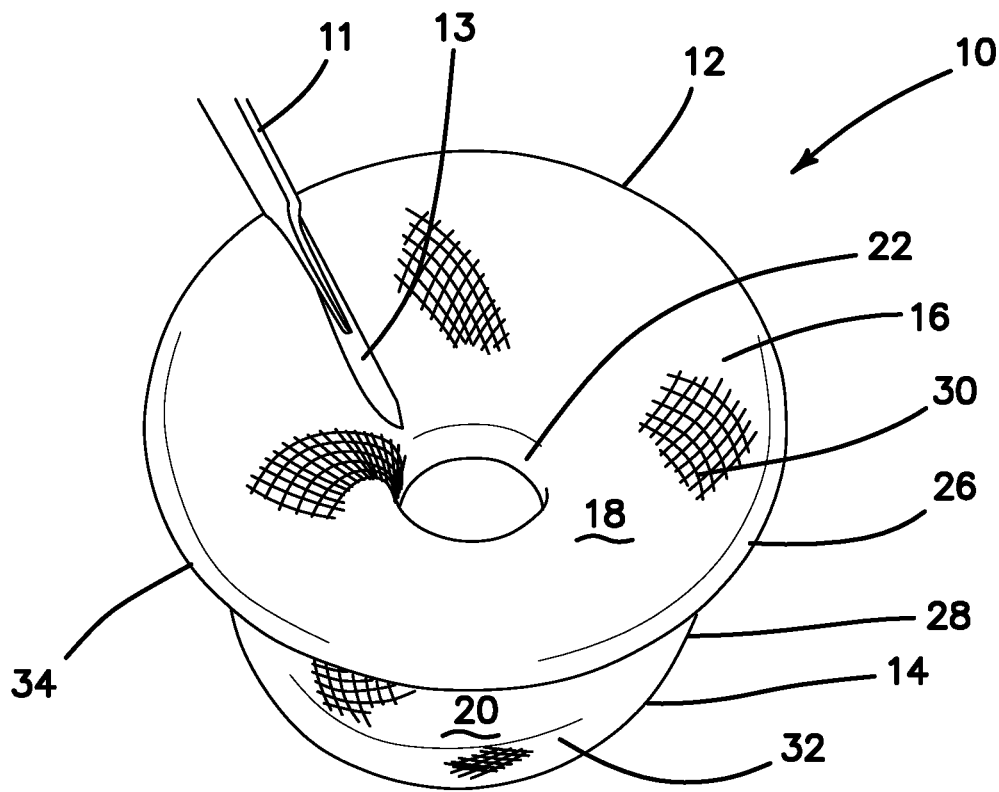
FIG. 1 is a top perspective view of a surgical scalpel and a mesh guard according to the present invention.
Figure 2:
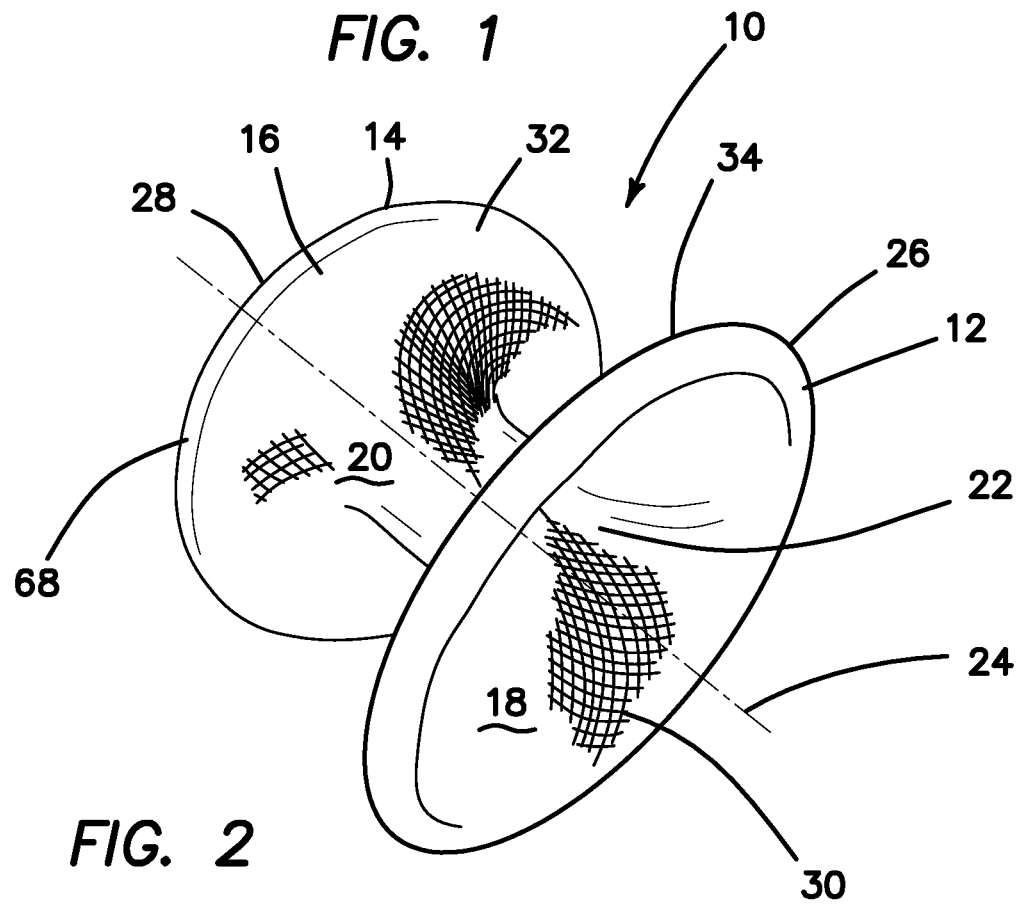
FIG. 2 is a top perspective view of a mesh guard according to the present invention.
Figure 3:
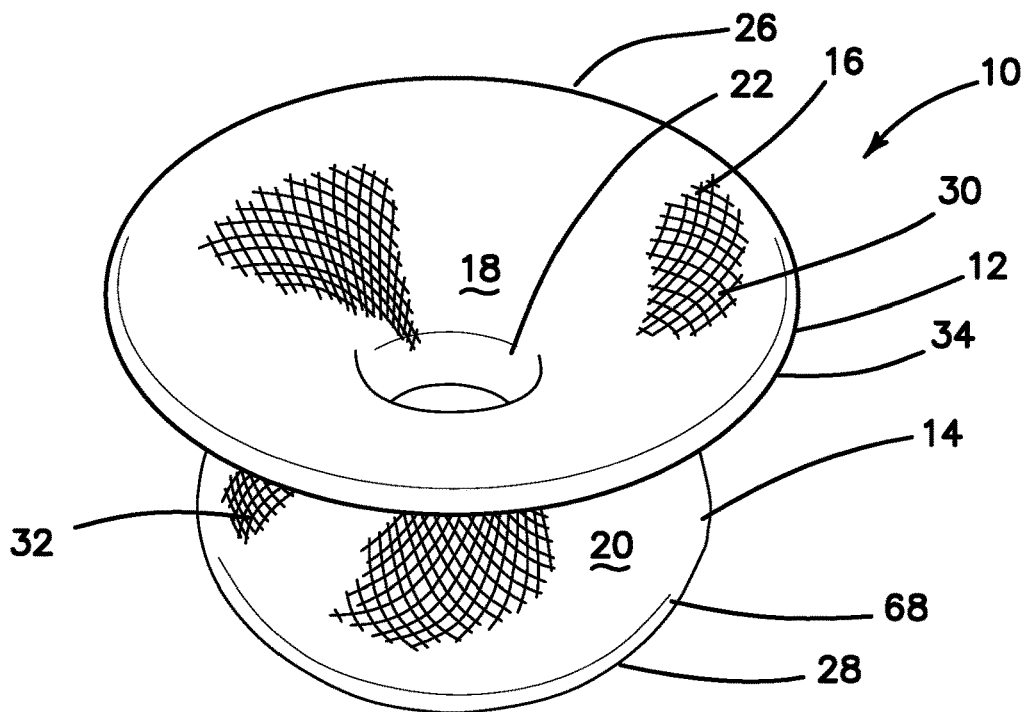
FIG. 3 is a top perspective view of a mesh guard according to the present invention.
Figure 4:
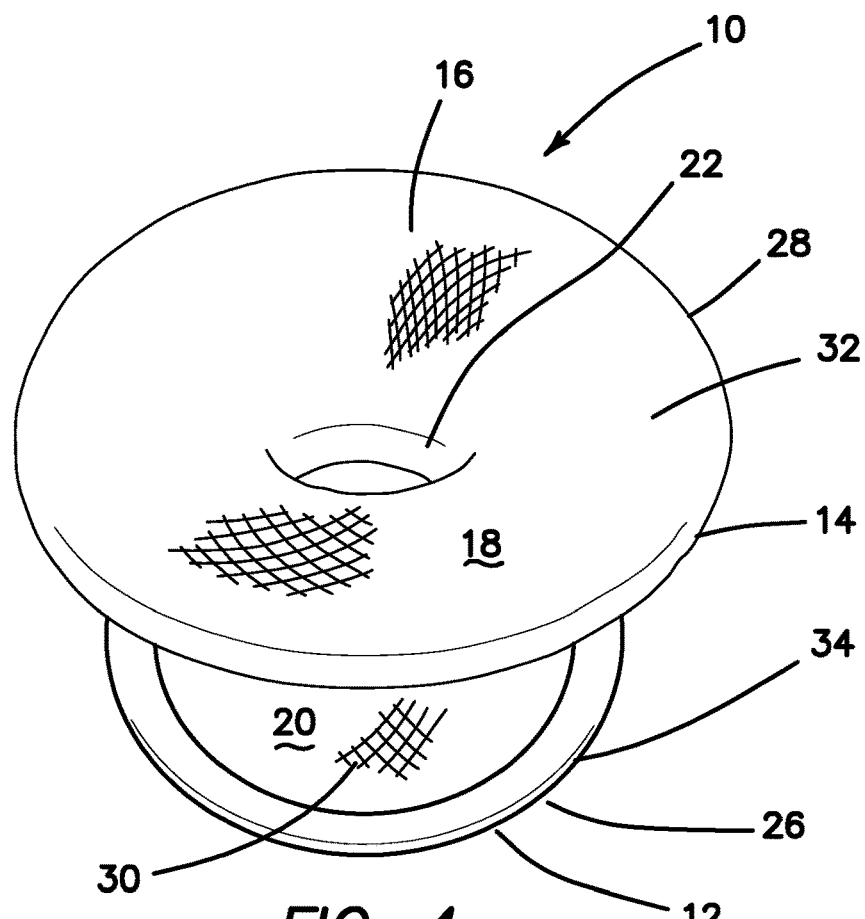
FIG. 4 is a bottom perspective view of a mesh guard according to the present invention.

Turning now to FIGS. 1-4, there is shown a mesh guard 10 according to the present invention. In FIG. 1, a surgical scalpel 11 with a sharp blade 13 is shown against the mesh guard 10 to illustrate the cut-resistant properties of the mesh guard 10. The mesh guard 10 includes a sidewall 16 that extends between a proximal end 12 and a distal end 14. The sidewall 16 has an inner surface 18 and an outer surface 20 and a thickness therebetween. The mesh guard 10 includes a central lumen 22 that extends along a longitudinal axis 24 between the proximal end 12 and the distal end 14. The central lumen 22 defines a proximal opening 26 at the proximal end 12 and a distal opening 28 at the distal end. The lateral dimension of the mesh guard 10 lies in planes perpendicular to the longitudinal axis 24.

At the proximal end 12, the mesh guard 10 has a flared, funnel-like, trumpet-like or horn-like shape formed by the sidewall 16 extending laterally outwardly away from the longitudinal axis 24 to form a smooth radial extension or top flange 30. Similarly, the distal end 14 also has a flared, funnel-like, trumpet-like or horn-like shape formed by the sidewall 16 extending laterally outwardly away from the longitudinal axis 24 to form a radial extension or bottom flange 32. The top flange 30 serves as an apron of protection when inserted into a body opening. The top flange 30 further acts as a cutting board surface against which tissue may be cut with a blade in confidence without damage to underlying, adjacent tissue, containment bag or retractor. The top flange 30 overlays the body at the margins of a body opening, orifice or incision site. If not used directly as a cutting surface, the top flange 30 serves as a protective backdrop to cutting taking place above the top flange 30, thereby, providing protection against a stray blade. In one variation, the top flange 30 includes a top lip 34 that turns downwardly toward the distal direction to form a smooth curved or rounded perimeter.

Furthermore, the top flange 30 and the bottom flange 32 serve as an anchor to help retain the mesh guard 10 in connection with the human body such that the mesh guard 10 stays in position and does not slip into or out of the body opening, orifice, or incision into which it is placed. The top flange 30 serves as an anchor to prevent the mesh guard 10 from moving distally into the body opening and the bottom flange 32 serves as an anchor to prevent the mesh guard from moving proximally out of the body opening. The mesh guard 10 is easily inserted by scrunching down or squeezing the bottom flange 32 by hand or instrument to reduce its lateral dimension, in particular, the lateral dimension of the bottom flange 32 as shown in FIG. 6 relative to the nominal, resting configuration shown in FIG. 5. The interstices between the mesh filaments provide space for the filaments to move closer together to reduce the lateral dimension of the distal end. Also, the distal end of the guard may be folded parallel to an axial direction because the mesh is highly flexible to further reduce the lateral dimension of the distal end.

Once placed inside a body opening, the mesh guard 10 serves as a protective portal into the body and/or across a body wall between inside a patient and outside the patient. The funnel-like shape of the bottom flange 32 at the distal end 14 also helps to lead or guide tissue into the central lumen 22 of the mesh guard 10 when tissue is being pulled through the central lumen 22 from inside the patient through the mesh guard 10 and out the proximal opening 26 outside the patient. Of course, the tissue may first be placed inside a containment bag inside the patient and the mesh guard 10 placed inside the containment bag across the body opening to serve as a portal from inside the containment bag to outside the containment bag. Tissue too large to be extracted through the body opening (e.g. orifice, incision) is reduced by cutting with a blade 11 with the mesh guard 10 in position so that the surrounding tissue, bag and retractor, if either one or more are used in conjunction with the guard 10, are protected. The smaller portions of tissue that were reduced in size by a blade 11 are then removed from the patient. The funnel-like shape of the top flange 30 at the proximal end 12 helps to safely guide needed instruments such as surgical graspers or blades into the central lumen 22 into the proximal opening 26 to perform the tissue reduction/morcellation without damaging any surrounding tissue, containment bag and/or retractor at the margin of the body opening. Of course, the body opening is used to describe any opening into the body of a patient and may include and is not limited to an opening created by an incision, and a natural orifice such as the vagina or anus. The mesh guard 10 need not be limited to use as a portal to inside the patient from outside the patient, but may also find application for use wholly inside the patient such as in portions of a bowel, colon, stomach and other organs, for example. In essence, the mesh guard 10 can be used wherever protection of tissue, and/or easily puncturable containment systems including bags and retractors, at the margins is desired.

Figure 5:
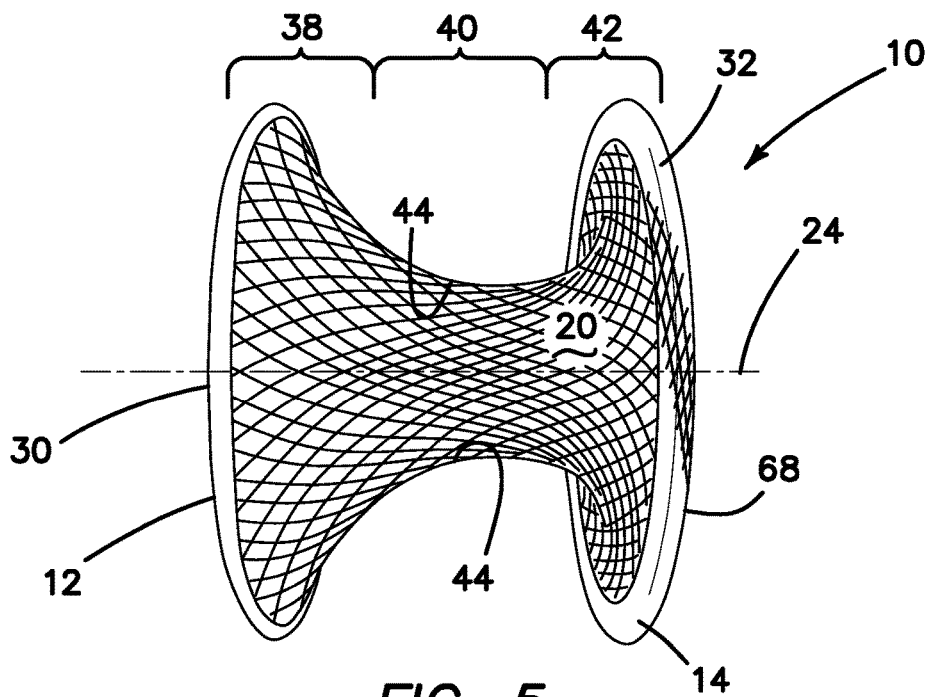
FIG. 5 is a side view of a mesh guard according to the present invention.
Figure 6:
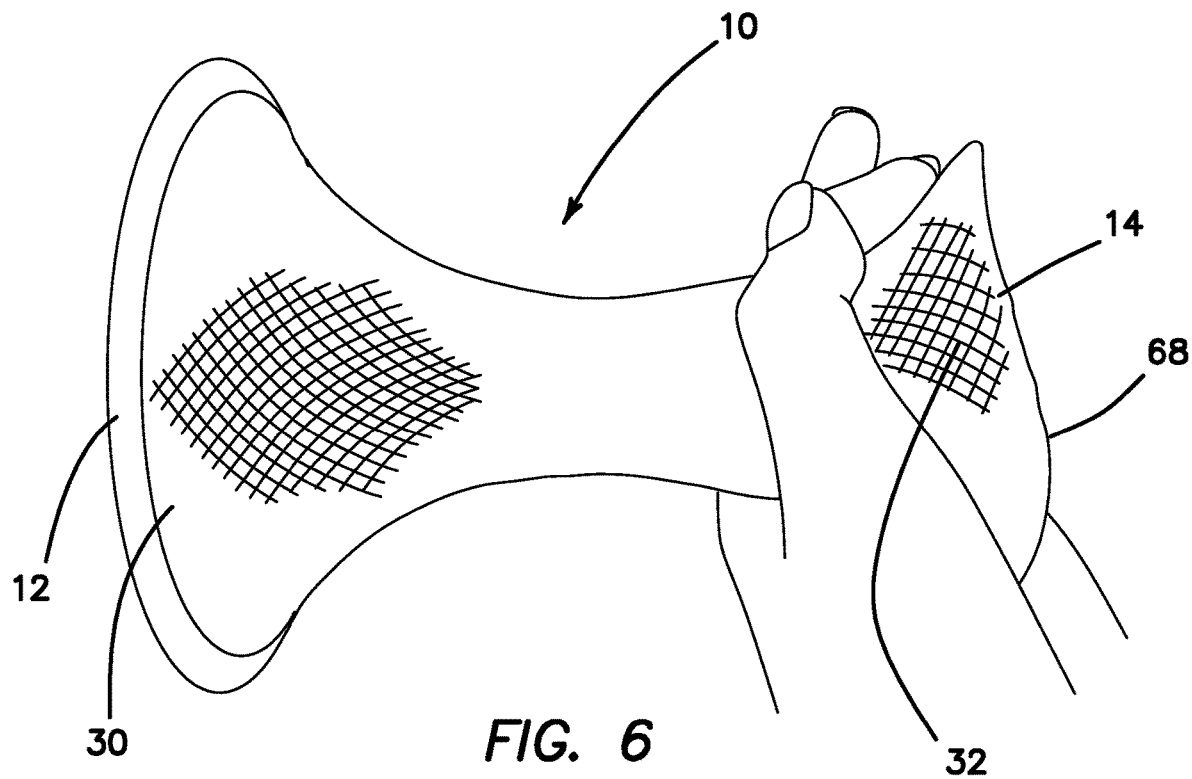
FIG. 6 is a side view of a mesh guard with the distal end compressed by a hand according to the present invention.

With reference to FIG. 5, the mesh guard 10 can be divided into approximately three interconnected sections including a proximal section 38 that includes the top flange 30, a midsection 40 that includes the smallest resting diameter or throat of the central lumen 22, and a distal section 42 that includes the bottom flange 32. The midsection 40 is located between the proximal section 38 and the distal section 42 along the longitudinal axis 24. The midsection 40 is located distally of the proximal section 38 and the distal section 42 is located distally of the midsection 40. All three sections 38, 40, 42 are integrally formed and the sidewall 16 transitions smoothly across all three sections 38, 40, 42. The central lumen 22 serves as a protected working channel for the passage of instruments and tissue specimens.

The mesh guard 10 has an hourglass-like shape wherein the outer surface 20 is curved and concave relative to the longitudinal axis 24. The outer surface, excluding any top lip 34 and bottom lip 36 is defined by any curve 44, such as including but not limited to a parabola, hyperbola, circular section, or elliptical section, having a single point of inflection transcribed by rotation about the longitudinal axis at a radial distance from the longitudinal axis to form the central lumen 22. In one variation, the point of inflection of the transcribed curved is located midway between the proximal end 12 and the distal end 14 making the mesh guard 30 vertically symmetrical. In other variations, the mesh guard 10 is not vertically symmetrical and the point of inflection may be located more proximally or more distally from the midpoint between the proximal end 12 and the distal end 14. For example, in FIG. 5, the point of inflection is located slightly distally from the midpoint near the distal end 14. The inner surface 18 conforms closely to the outer surface 20 and is curved and convex relative to the longitudinal axis 24. In one variation of the mesh guard 10, the sidewall 16 at the midsection 40 includes a substantially straight portion and is not curved or is slightly curved and the inner surface 18 and the outer surface 20 are substantially parallel to the longitudinal axis 24. In the variation shown in FIGS. 1-6, the sidewall 16 has a more aggressive curvature near the distal end, that is, the rate of change of the curve 44 near the distal end is greater than the rate of change of the curve near the proximal end 12. The aggressive curve 44 at the distal end 14 provides for stronger anchoring properties needed at the distal end 14. Also, the aggressive curve 44 at the distal end 14 helps keep the walls of a containment bag out of the way. When the mesh guard 10 is placed in a containment bag, the bottom flange 32 will expand outwardly and deflect with it any portion of the containment bag that is near or in contact with the guard.

It can be said that the geometry of the mesh guard 30 closely resembles a cooling tower. The shape can be generalized to a hyperboloid, a surface of revolution about a given axis with a defined height. Three main radii can be used to describe the shape: the radius at the proximal end 12 (RP), the radius at the distal end 14 (RD) and the radius at the throat (RT) where the height of RT lies between the height of RD and the height of RP along the vertical axis. The throat can be further defined as the region of the midsection having the smallest resting diameter or where the curves of different hyperboloids meet. To account for the thickness of the sidewall 16, the inner and outer radius is defined for any number of layers of mesh therebetween. Furthermore, the surface of revolution may be defined by one or more curves joined together to form a smooth transition. For example, the proximal section 38 may be defined by a first curve of revolution, the midsection 40 defined by a second curve or line of revolution to form a cylindrical section, and the distal section 42 defined by a third curve or revolution that may be the same as or different from the first curve. Hence, there may be three points of inflection, one for each curve, for the length of the sidewall 16.

When the mesh guard 10 is in an unstressed and resting position, the central lumen 22 is substantially circular in a plane perpendicular to the longitudinal axis 24. The mesh guard 10 may also be molded to have an elongated, elliptical, oval central lumen 22. The central lumen 22 has the smallest diameter at the midsection 40. From the smallest resting diameter at the midsection 40, successively proximal cross-sections of the mesh guard 10 taken perpendicular to the longitudinal axis 24 define circles having progressively increasing diameters towards the proximal end 12. While in a resting configuration, successively distal cross-sections of the mesh guard 10 taken perpendicular to the longitudinal axis 24 define circles having progressively increasing diameters from the smallest resting diameter at the midsection 40 towards the distal end 14. Hence, the mesh guard 10 is narrow in the middle and wide at its proximal and distal ends 12, 14. The mesh guard 10 is substantially symmetric about the longitudinal axis 24 when in its resting configuration.

Figure 7:
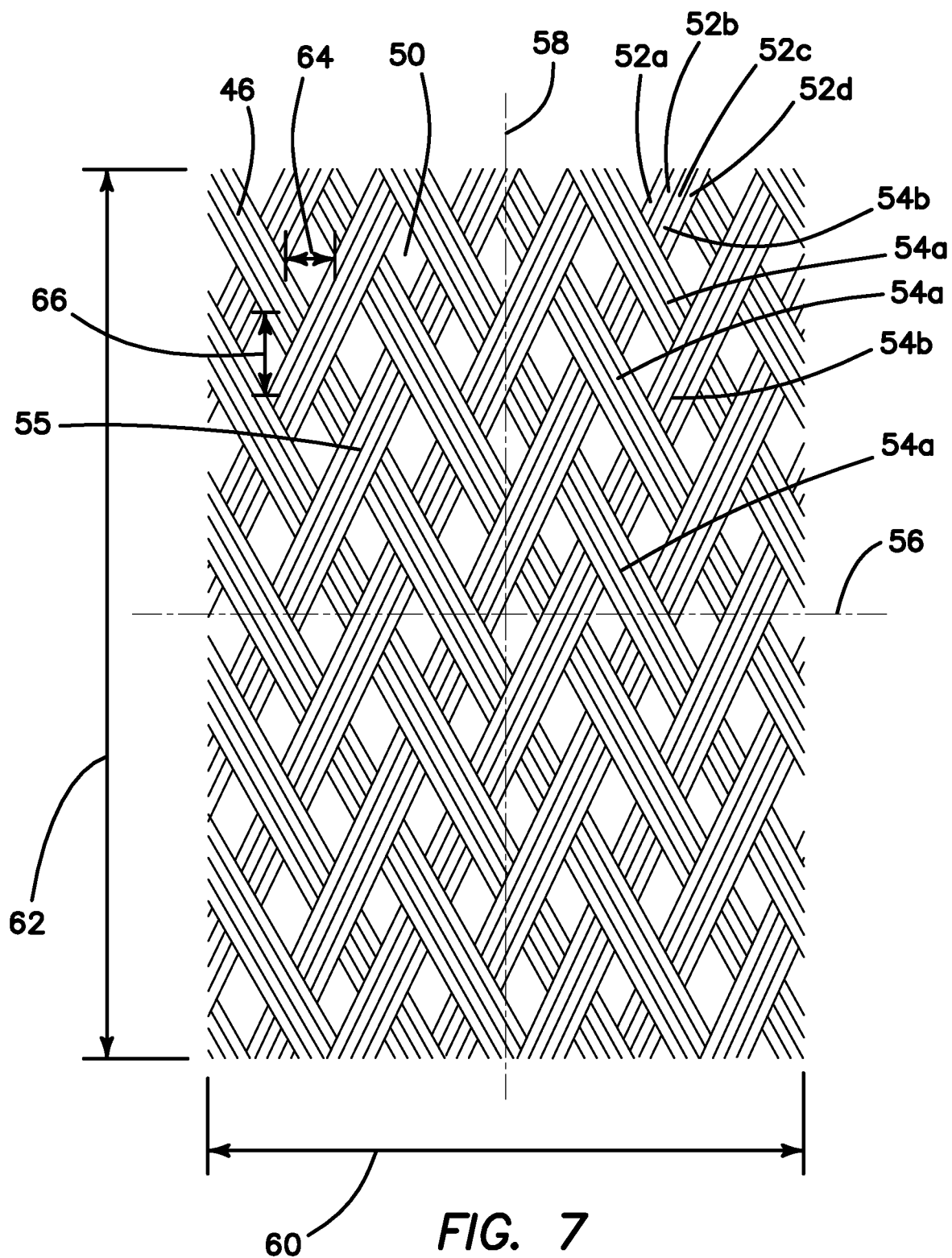
FIG. 7 is a partial sectional view of one layer of a mesh braid of a sidewall of a mesh guard according to the present invention.
Figure 8:
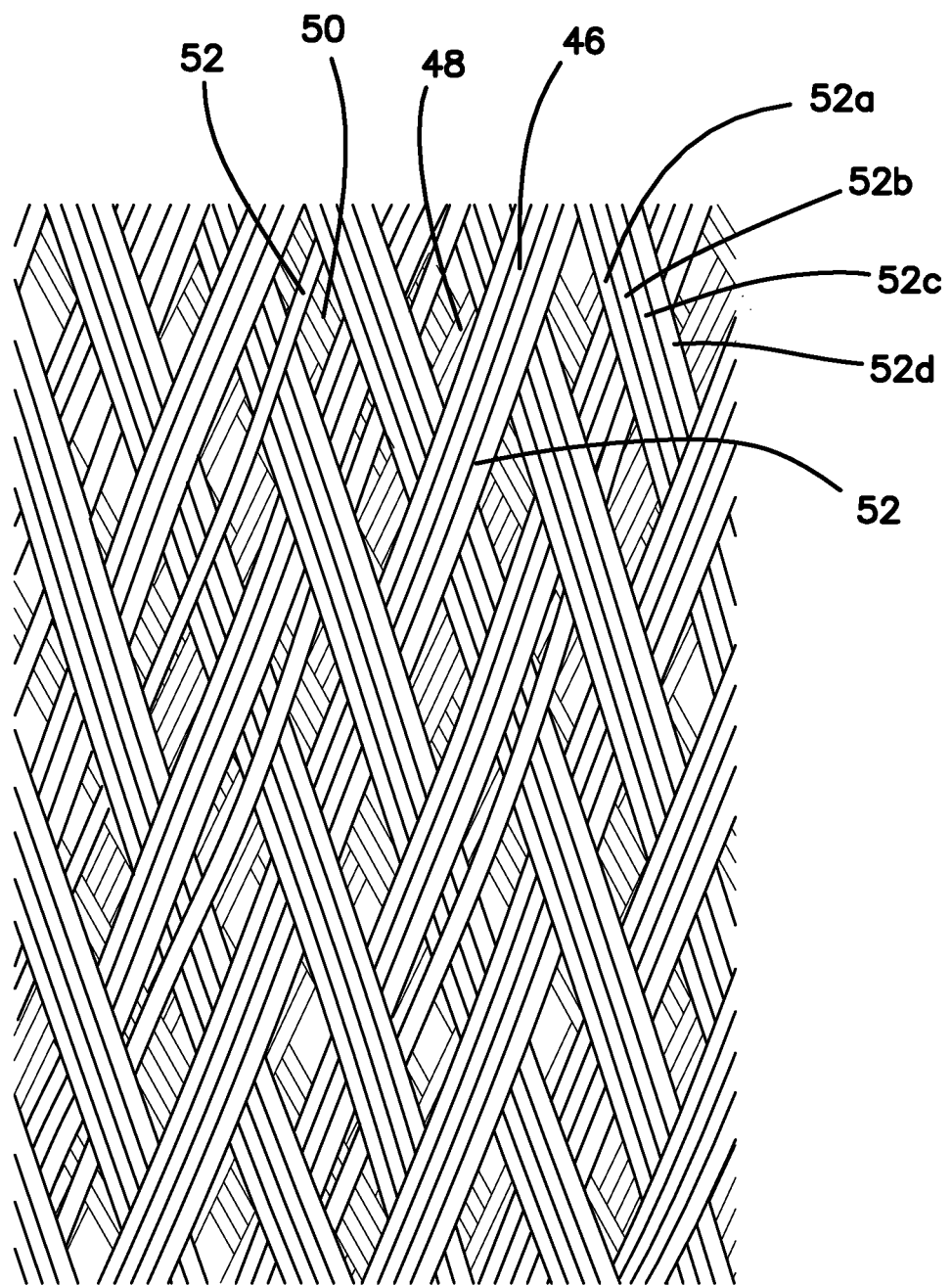
FIG. 8 is a partial sectional view of two layers of a mesh braid of a sidewall of a mesh guard according to the present invention.

The mesh guard 10 is made of mesh. In one variation, the entire sidewall 16 of the mesh guard 10 from the proximal end 12 to the distal end 14 is made of a mesh material. In one variation, the sidewall 16 is made of a single first layer 46 of mesh material as shown in FIG. 7. In another variation, the sidewall 16 is made of a first layer 46 of mesh material that overlaps a second layer 48 of mesh material as shown in FIG. 8. FIG. 7 is an exemplary layer 46 of mesh material. The mesh is an interwoven or intertwined braid or network of grouped or ungrouped interlocking filaments 52 creating an open texture structure with small substantially uniform windows/interstices 50. The circumferential surface of the sidewall 16 is made up of a number of mutually offset filamentary elements which are braided together to form a braid with a multiplicity of polygonal cells. The braid can be constructed such that two intersecting systems of filamentary elements are interlaced so that each filamentary element of one system is alternately guided over and under each filamentary element of the other system. Such a pattern of the braid is referred to as a plain weave.

With reference still to FIGS. 6-7, four mono-filaments 52a, 52b, 52c, 52d are grouped into a single strand or band 54. Each band 54 is woven under and over one or more other bands 54 at an angle. For example, in FIG. 7, a plurality of parallel bands 54a that are angled in a first direction are interwoven with a plurality of parallel bands 54b that are angled relative to the first direction. Each band 54a, 54b contains four filaments 52a, 52b, 52c, 52d. The mesh layer 46 is woven such that each band 54a passes underneath or intersects two consecutively adjacent bands 54b before passing above or intersecting the following two consecutive bands 54b. Each band may pass underneath one or more adjacent bands before passing over the following one or more band. The weave forms a plurality of quadrilateral substantially rhomboid windows 50 therebetween with band intersections 55 at the apexes. The number of intersections 55 within a unit length of measure defines the density of the weave. More intersections 55 make the weave tighter and the size of the windows 50 becomes smaller. The second layer 48 of mesh material at least overlaps and partially closes some or all of the windows 50 to provide greater protection as shown in FIG. 8. Also, the entire length of the sidewall comprises a double wall. In other variations, only a part of the sidewall is double-walled mesh and the other part is single-walled mesh to provide greater flexibility. Because of the weave arrangement and density, the mesh material can stretch along the lateral axis 56 as the bands 54 can slide over and relative to each other making the windows 50 larger in size. Widening of the mesh when stretched laterally reduces the length 62 of the mesh layer 46. The mesh material can also stretch along the longitudinal axis 58 of the mesh. Lengthening of the mesh when stretched longitudinally reduces the width 60 of the mesh layer 46. The amount of stretch for the first layer 46 in the lateral direction 48 is greater than the amount of stretch that the first layer 46 is capable of in the longitudinal direction 50. Each window 50 has a width measured along the lateral axis 56 and a window length 66 measured along the longitudinal axis 58. Stretching of the mesh in the lateral direction 56 is in part limited by the sum of the widths 64 of the windows 50 along the lateral direction 56 and stretching of the mesh in the longitudinal direction 58 is limited by the sum of the lengths 66 of the windows 50. Because the length 66 of the window 50 is longer than the width 64 of the window 50, the mesh will stretch more in the lateral direction 56. Hence, for the mesh pictured, the dominant direction of stretch is along the lateral axis 56 of the mesh. The second layer 48 of mesh material is of the same density as the first layer 46 and is oriented in the same direction when overlaid. The second layer 48 is the same as the first layer 46. The weave density is dense enough to prevent a blade such as a scalpel from penetrating and loose enough so that the mesh is still flexible and capable of stretching. Stretching of the mesh guard in the lateral direction is often accompanied by a reduction in the length of the guard along the longitudinal axis as the longitudinal dimension of the windows is reduced by the stretching action.

The mesh guard 10 is constructed such that the mesh sidewall has a dominant direction of stretch that is perpendicular to the longitudinal axis 24 of the mesh guard 10. In this arrangement, the central lumen 22 of the mesh guard 10 is free to stretch open and enlarge uniformly, conformingly, or irregularly around the circumference. Also, the central lumen 22 can be reduced in size in the lateral direction to a smaller diameter when the incision or body opening is smaller. Expansion in the lateral direction advantageously permits larger specimens to pass through the central lumen 22 while still providing protection to the surrounding tissue. After the stretch forces are released, the sidewall 16 is biased toward its resting configuration and will spring back. When any latitudinal extensions forces act on the guard 10, it relaxes elastically into its original width on account of its cell-like weave structures. Hence, the central lumen 22 is self-adjusting. For example, when in the vaginal canal, the mesh guard 10 accommodates for different female anatomy. The central lumen is able to adjust to how narrow or wide the patient's vagina is. The central lumen is also able to stretch and increase in diameter as described above to accommodate varying size uteri intended to be extracted in a hysterectomy. When placed inside an abdominal incision, for example, the mesh guard 10 conforms to and can accommodate for varying incision sizes. Hence, the mesh sidewall 16 can readily expand and stretch in the radial direction perpendicular to the longitudinal axis 24 as well as be compressed to close the throat diameter either by reducing the throat diameter or by creating a longitudinal fold or vertical wrinkle. This ability permits the sidewall to conform to anatomy as well as to be selectively deformed by the user such as for insertion purposes and/or for purposes of accommodating various body opening lengths. For example, FIG. 6 illustrates the mesh guard being deformed by the user at the distal end 14 for insertion through a body opening. Also, the configuration shown in FIG. 6 is also illustrative of an exemplary inserted configuration of the guard that has been inserted into a vagina and in which it has conformed to longer body opening such as a longer vagina with the bottom flange 32 still providing anchoring characteristics relative to the length and width of the guard shown in FIG. 5. In the hypothetical inserted configuration shown in FIG. 6, the mesh guard 10 is longer than its resting undeformed configuration shown in FIG. 5. Hence, the guard 10 advantageously can be increased in length and width as well as be reduced in length and width to less than its resting configuration. When released, the mesh guard 10 pops back to its resting undeformed configuration of FIG. 5.

Each filament 52 has a cross-sectional shape that is circular; however, other shapes, including to but not limited to oval, elongate, and rectangular, are within the scope of the present invention. Each filament 52 is cylindrical in shape and has a diameter of approximately 0.01-0.02 inches. The mesh is made of any biocompatible polymer such as resin, polyester and nylon. The mesh can also be made of any biocompatible metal such as nitinol. In one variation, the filament 52 is made of polyethylene terephthalate.

The mesh guard 10 is manufactured by providing a sleeve or tube of mesh material. For example, FLEXO® Original braided sleeve by Techflex in Sparta, N.J. is employed. The tubular sleeve has an open proximal end and an open distal end. The sleeve is braided from 10 mil polyethylene terephthalate (PET) monofilament yarns. The material has a wide operating temperature range, is resistant to chemical degradation, UV radiation and abrasion. The material is capable of being heat set, heat formed, is flexible, has low or zero moisture absorbance, is biocompatible, and has a high abrasion resistance. The sleeve has a nominal resting diameter size anywhere in the range of approximately 1.75-2.75 inches. However, dependent upon the application of use of the guard, a larger or smaller nominal diameter sleeve can be selected. Also, the manufacturing process of forming the guard by heating may result in the guard having a nominal resting diameter that varies along its length and may be larger or smaller than the selected nominal diameter of the sleeve from which it is made. If a two-inch nominal diameter sleeve is selected, it has an expansion range between a minimum expansion of approximately 1.5 inches and a maximum expansion of approximately 3.5 inches in the lateral direction 56. The resting nominal expansion is approximately 2.0 inches. A tighter weave for a two-inch nominal size diameter may be selected. For the tighter or higher density weave, the expansion range is between a minimum expansion of approximately 1.75 inches and a maximum expansion of 3.125 inches. The resting nominal expansion is approximately 2.0 inches. Each window or cell a resting inner dimension of approximately equal to or less than 2 millimeters, along the longitudinal axis, lateral axis or perpendicular thereto. In another variation, the resting inner dimension of a window/cell is approximately equal to or less than 1 millimeter measured along the longitudinal axis, lateral axis or perpendicular thereto. Depending upon the desired flexibility and expansion characteristics, the desired density weave may be selected.

After the desired mesh sleeve is selected, the desired length of the guard 10 is ascertained and the mesh sleeve is cut such as with scissors, a hot knife, soldering iron, or hot wire. The length of the sleeve is approximately a little longer than two times the desired length of the final mesh guard. One end of the mesh sleeve is turned or tucked into the lumen of sleeve and rolled down such that the mesh sleeve overlaps onto itself forming a double wall structure. Alternatively, one end of the mesh sleeve is turned outwardly instead of inwardly into the lumen of the sleeve. Either way, if the sleeve is tucked inwardly or outwardly, the sleeve is rolled down. The result is a double-layered tube with a fold 68 formed at one end of the guard 10 which can be seen in FIGS. 2, 3 and 5. The other end will have the two free ends of the sleeve approximately side-by-side. The free ends of the sleeve will begin to fray as the braid unravels and filaments splay apart. Adhesive such as LOCTITE sealant may be applied to the ends of the mesh sleeve to prevent fraying of the filaments 52. Also, a hot knife may be used to reduce fraying. Further encasement and sealing of the filament ends at the proximal end of the guard will be described in detail below. The fold 68 is provided at the distal end 14 of the guard 10 as it forms a nice rolled lip without any exposed filaments 52 that may abrade tissue during use.

Figure 9:
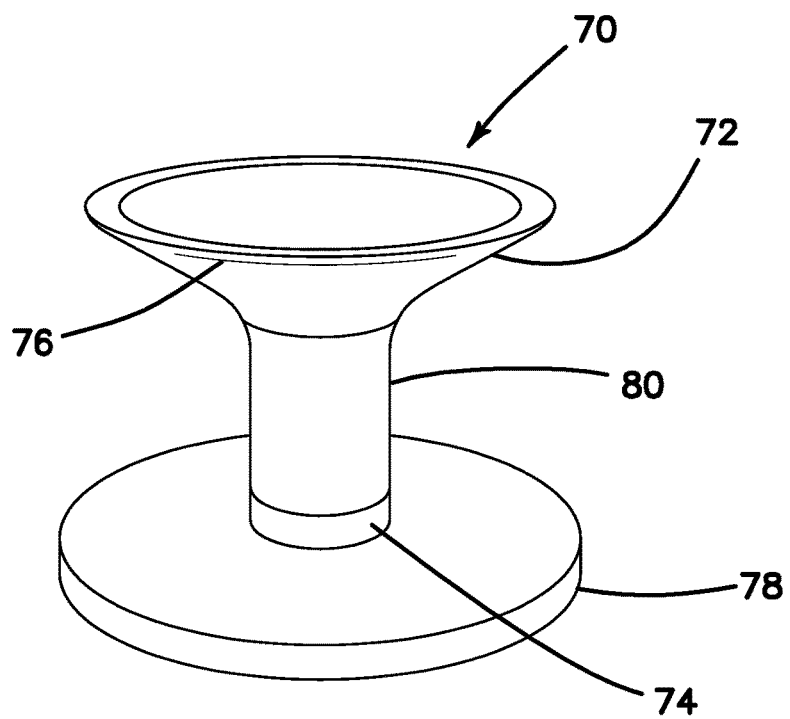
FIG. 9 is a top perspective view of a mold for a mesh guard according to the present invention.
Figure 10:
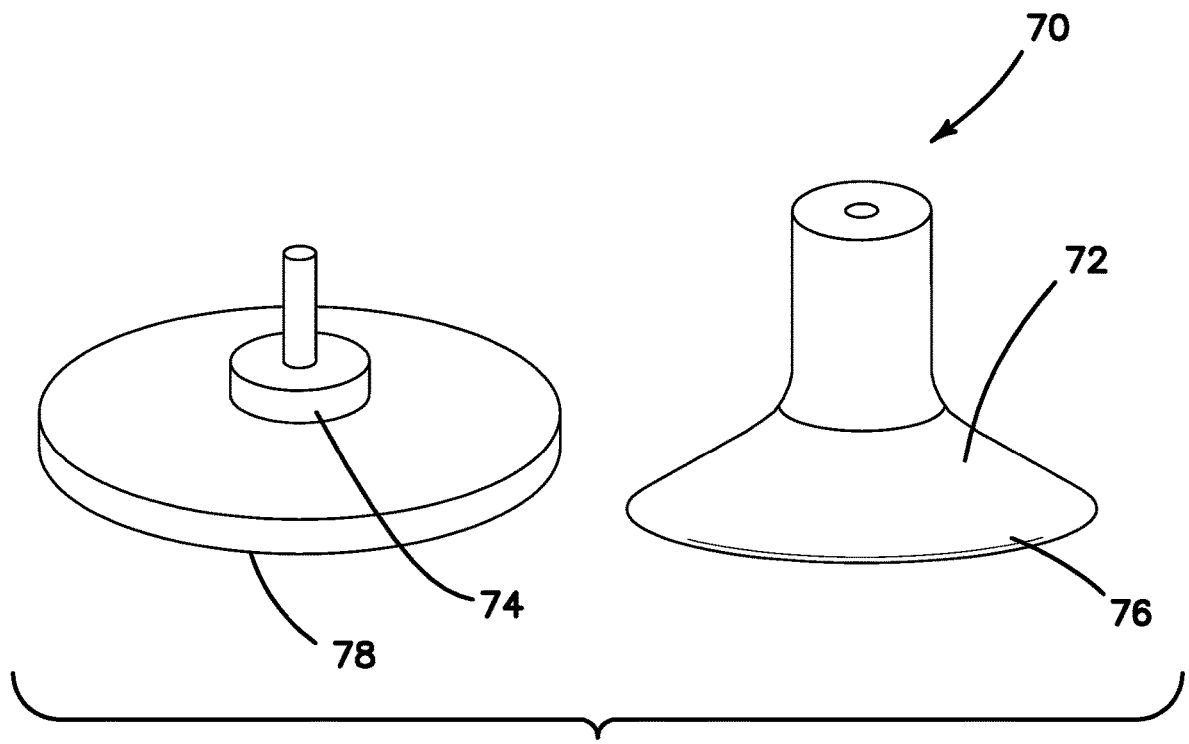
FIG. 10 is a top perspective view of a two-part mold for a mesh guard according to the present invention.
Figure 11:
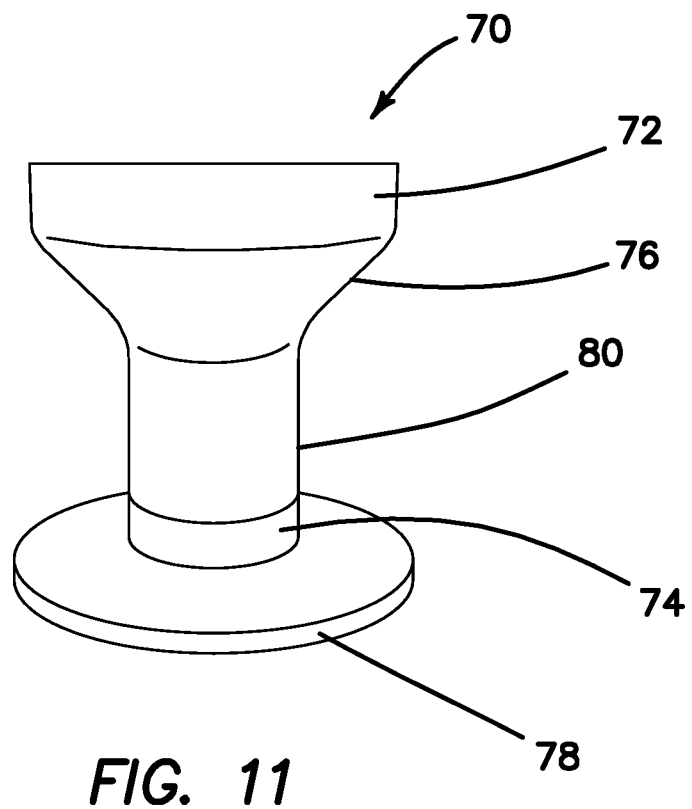
FIG. 11 is a top perspective view of a mold for a mesh guard according to the present invention.
Figure 12:
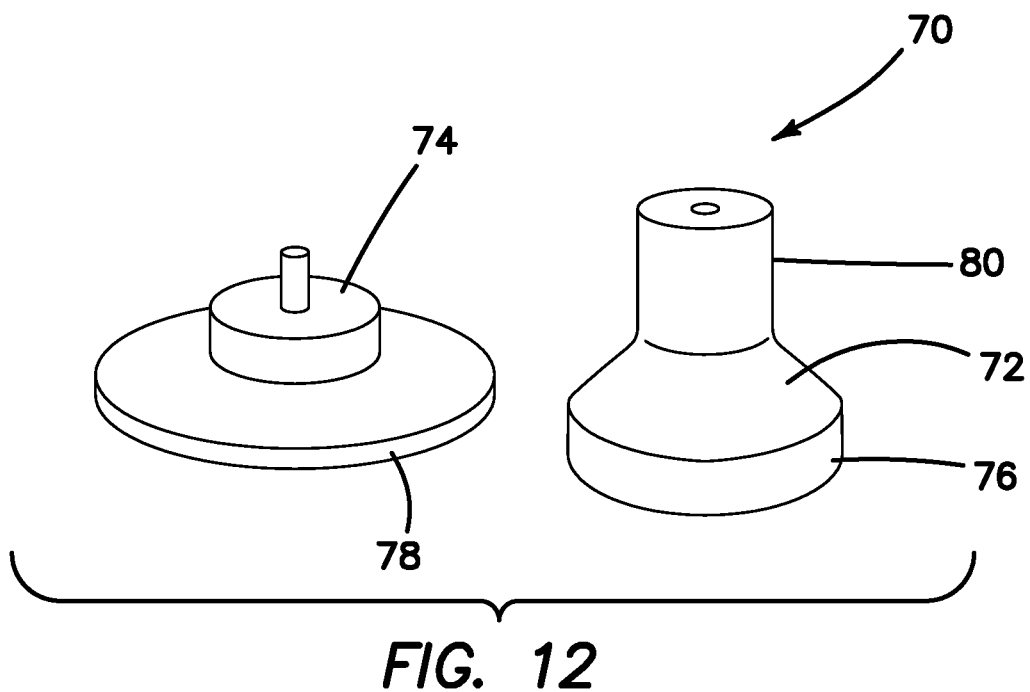
FIG. 12 is a top perspective view of a two-part mold for a mesh guard according to the present invention.
Figure 13:
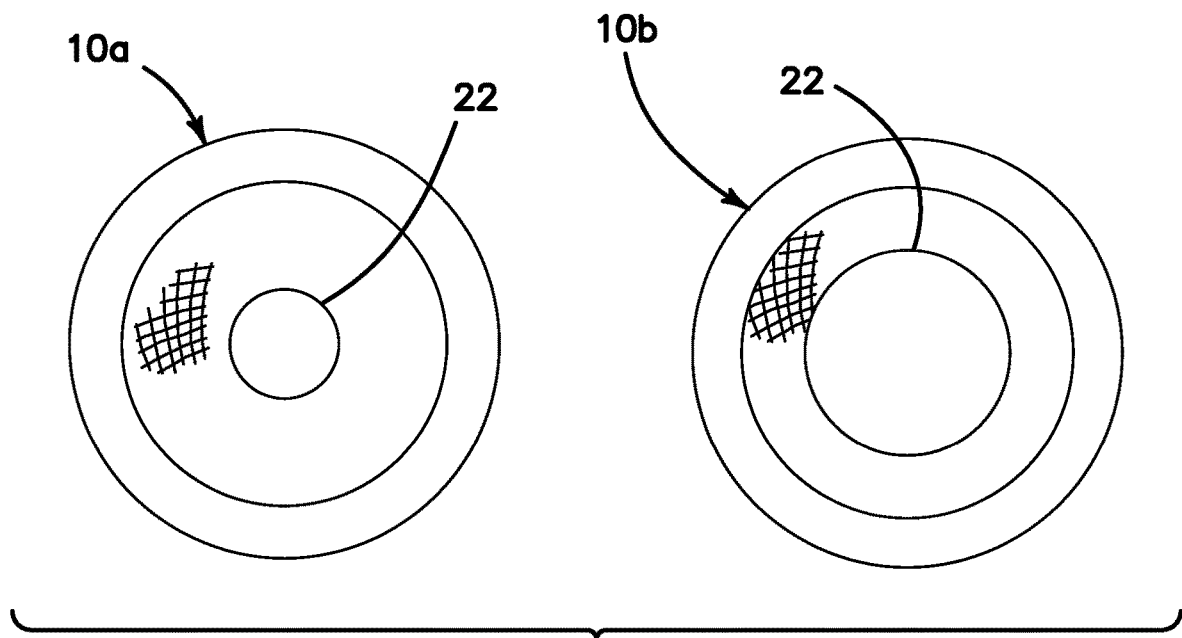
FIG. 13 is a top view of two mesh guards with different lumen diameters at the narrowest section along the longitudinal axis according to the present invention.
Figure 14:
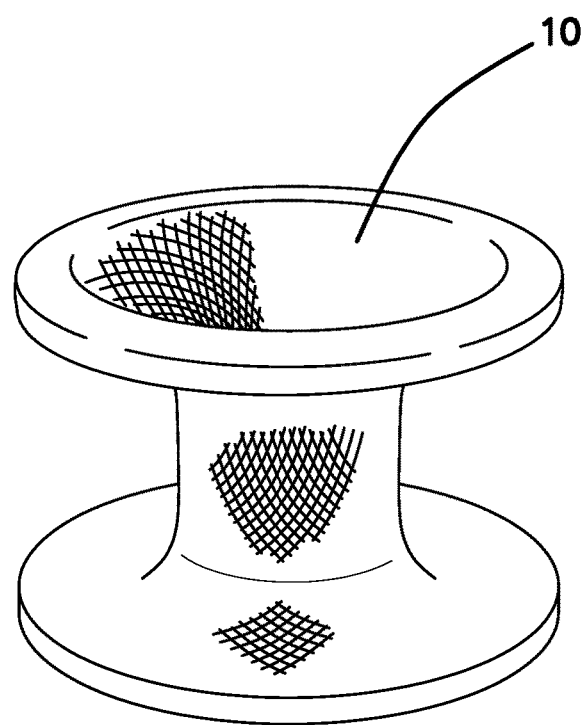
FIG. 14 is a top perspective view of a mesh guard according to the present invention.

Turning now to FIGS. 9-12, a mandrel 70 for forming the guard 10 is shown. The mandrel 70 includes a first part 72 and a second part 74 that are removably interconnected. The first part 72 includes a first flared flange 76 and the second part 74 includes a second flared flange 78. The mandrel 70 includes a neck portion interconnecting the first flange 76 and the second flange 78. The first part 72 of the mandrel 70 is disconnected by unscrewing it from the second part 74 of the mandrel 70 as shown in FIGS. 10 and 12 to facilitate mounting the mesh sleeve onto the mandrel 72. The two parts 72, 74 are reconnected after the mesh sleeve is in position on the mandrel 70. The mandrel 70 and the mesh sleeve are placed into an oven at a temperature of approximately 160 Celsius for about one hour. Less time is required in the oven if a higher temperature is used and a longer time is needed in the oven if a lower temperature is used. A thermosetting polymer is generally employed and it is heated to a glass transition temperature of the polymer. The heat will plastically deform the filaments 52 such that the mesh sleeve conforms around mandrel 70 assuming the shape of the mandrel 70 and heat set thereto. The filaments will retain the new shape corresponding to the mandrel shape when the mesh returns to room temperature. This heat settability or memory retention of the mesh material allows it to form the hourglass shape which when deformed springs back to its retained shape when released. One or more heat guns/lamps may be directed at the mesh sleeve on the mandrel 70 instead of or in addition to placing the mandrel and mesh sleeve in the oven. Once cooled, the mesh sleeve is removed from the mandrel 70 by disassembling the mandrel parts 72, 74. FIGS. 9-10 illustrate a mandrel 70 having a narrower neck portion 80 relative to the wider neck portion of the mandrel 70 shown in FIGS. 11-12. The resulting differences in the size of the central lumen 22 is shown in FIG. 13 wherein the mesh guard 10a on the lefts side is made with a mandrel 70 having a narrower neck portion 80 such as shown in FIGS. 9-10 and the mesh guard 10b on the right side is made with a mandrel 70 having a wider neck portion 80 such as shown in FIGS. 11-12. A smaller mandrel can be used to make a smaller mesh guard 10 such as the one shown in FIG. 14. The mesh guard 10 of FIG. 14 is suitable for placement across an abdominal incision, for example. For an abdominal guard, the guard 10 is sized and configured to accommodate incision sites that are approximately 1.5-7.0 centimeters wide. For a vaginal guard, the guard 10 is sized and configured to accommodate diameters of approximately 0.75-3.5 inches. The guard is approximately 2.5-3.0 inches long in its resting configuration.

After the mesh guard 10 has cooled and been removed from the mandrel 70, it is prepared for an optional dispersion coating. The mesh guard 10 is cleaned with isopropyl alcohol to insure that a dispersion coating will adhere to the mesh. The proximal end 12 and top flange 30 are dipped into a dispersion material of silicone and/or urethane. Alternatively, the proximal end 12 and top flange 30 are placed into a casting dish and dispersion material is poured into the casting dish. The dispersion coating enters, fills, covers and coats the filaments 52 and windows 50 of the dipped portion of the guard. The guard may be dipped more than once to create a desired coating. The guard 10 is allowed to completely dry. The mesh guard 10 may further or alternatively coated with an antimicrobial coating. The dispersion coating makes the dipped portion of the guard more rigid, stronger and more resistant to cutting. Dipping of the proximal end of the guard 10 is desirable to provide a reinforced flange for cut-resistant purposes. Also, the proximal end of the guard does not have to be squeezed or reduced in size for inserting into a body opening in application in which the proximal end of the guard resides outside of the body opening, making it more suitable for dispersion material.

Figure 15:
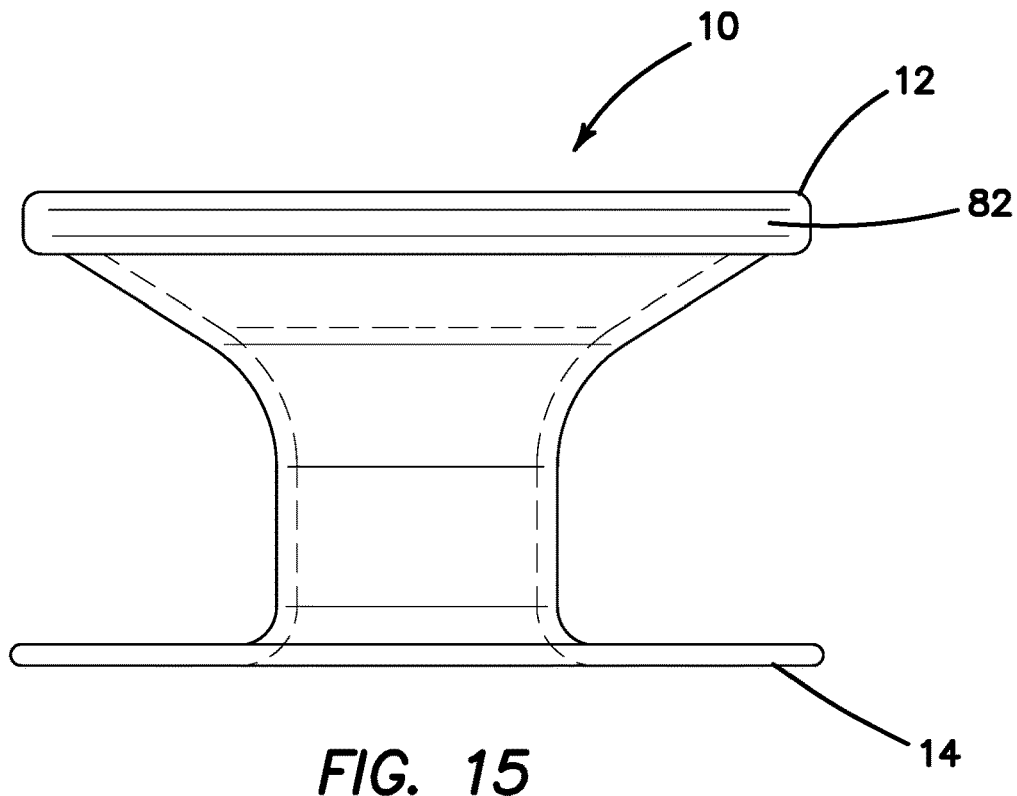
FIG. 15 is a side view of a mesh guard with an injection molded proximal ring according to the present invention.
Figure 16:
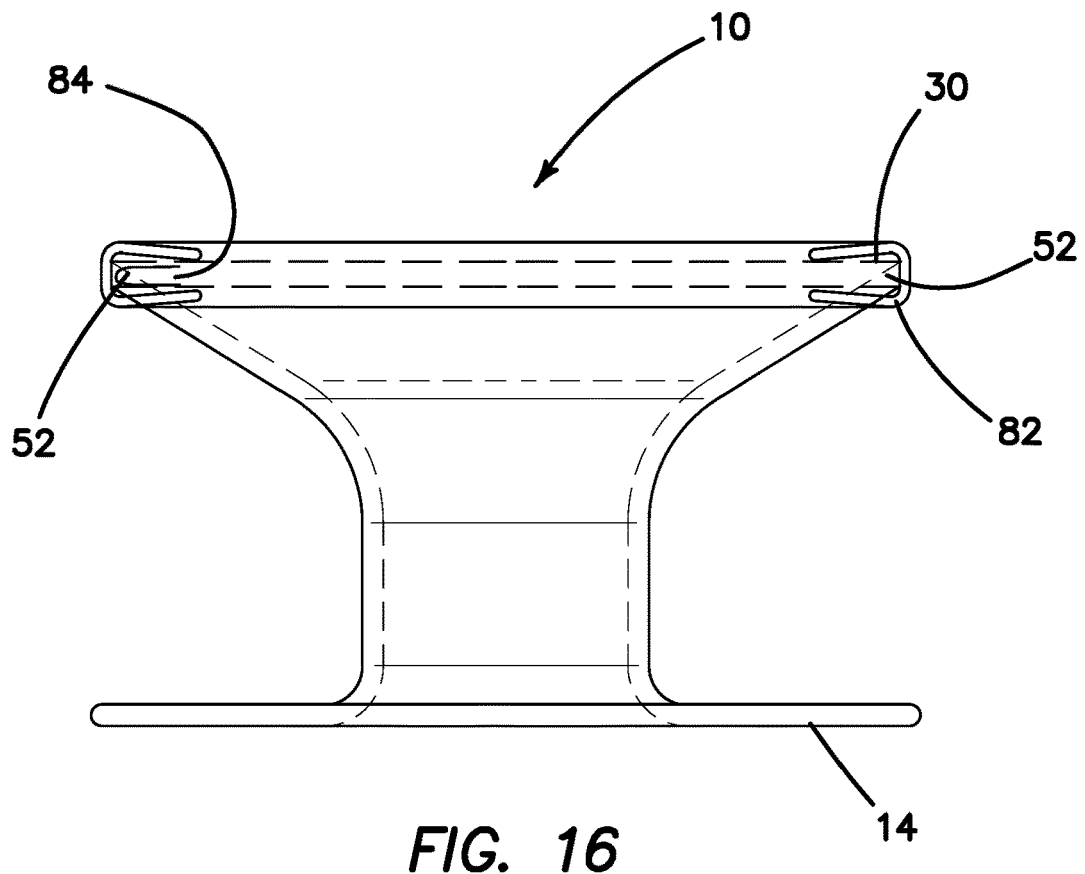
FIG. 16 is a cross-sectional side view of a mesh guard with an injection molded proximal ring according to the present invention.
Figure 17:
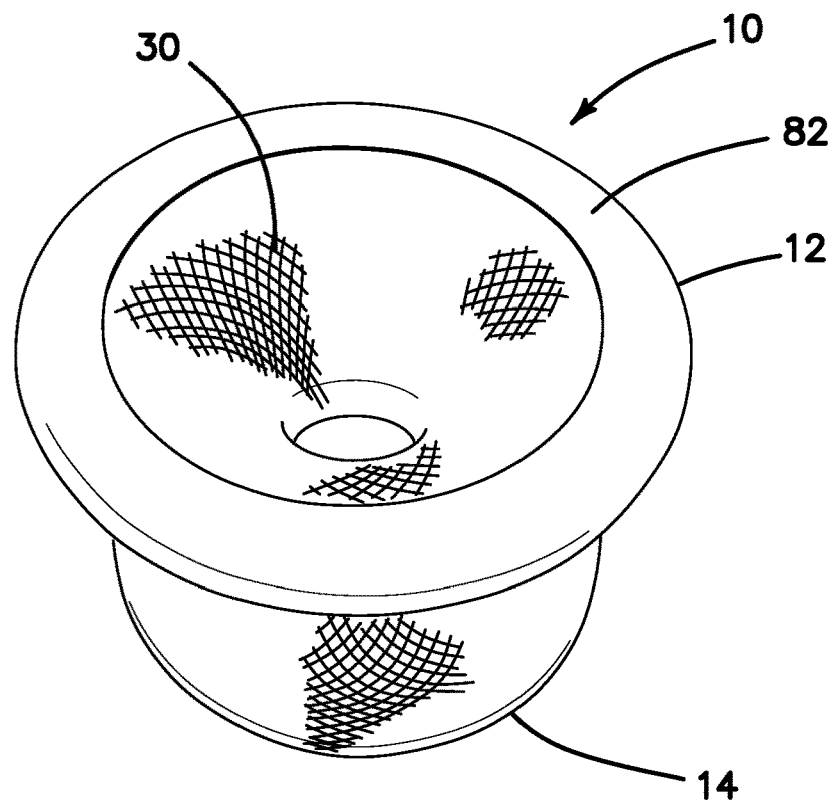
FIG. 17 is a top perspective view of a mesh guard with an injection molded proximal ring according to the present invention.

Turning now to FIGS. 15-17, there is shown a mesh guard 10 with an injection molded ring 82. The ring 82 is attached to the top flange 30 at the proximal end 12. The ring 82 is sized and configured to circumferentially encompass the proximal end to cover and contain the free ends of the filaments 52 and to prevent any fraying of the loose filament ends, covering any exposed filaments to prevent abrasion of the surroundings. The ring 82 is made of polymeric material and may be rigid or flexible. The ring 82 has a smooth outer surface and a channel 84 formed by the inner surface of the ring 82. The ring 82 is formed by injection molding. Adhesive or sealant is placed inside the channel 84 of the ring 82. The proximal end 12 of the mesh guard 10 including any free filament ends, frayed or loose filaments 52 are tucked into the channel 84 of the ring 82. The adhesive is allowed to cure and the ring 82 remains attached to the mesh guard 10. The ring 82 not only captures and contains the filaments 52 at their free end, but also, the ring 82 provides added rigidity and protection at the proximal end because of the guard otherwise being made entirely of flexible mesh.

Figure 18:
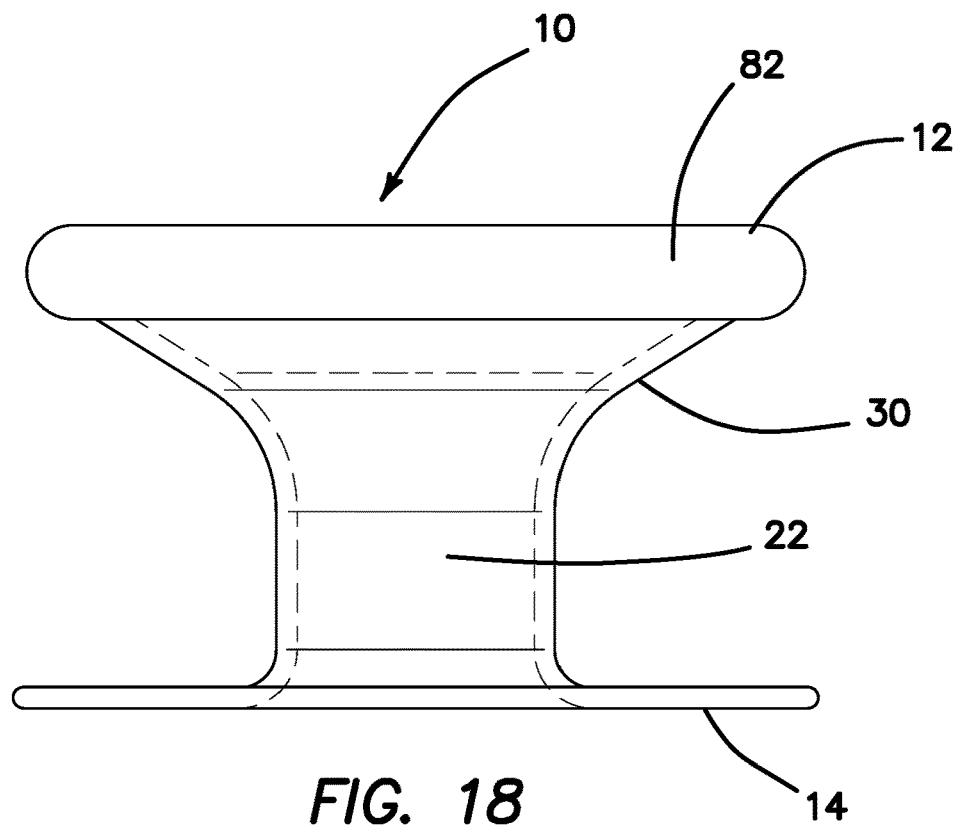
FIG. 18 is a side view of a mesh guard with an extruded proximal ring according to the present invention.
Figure 19:
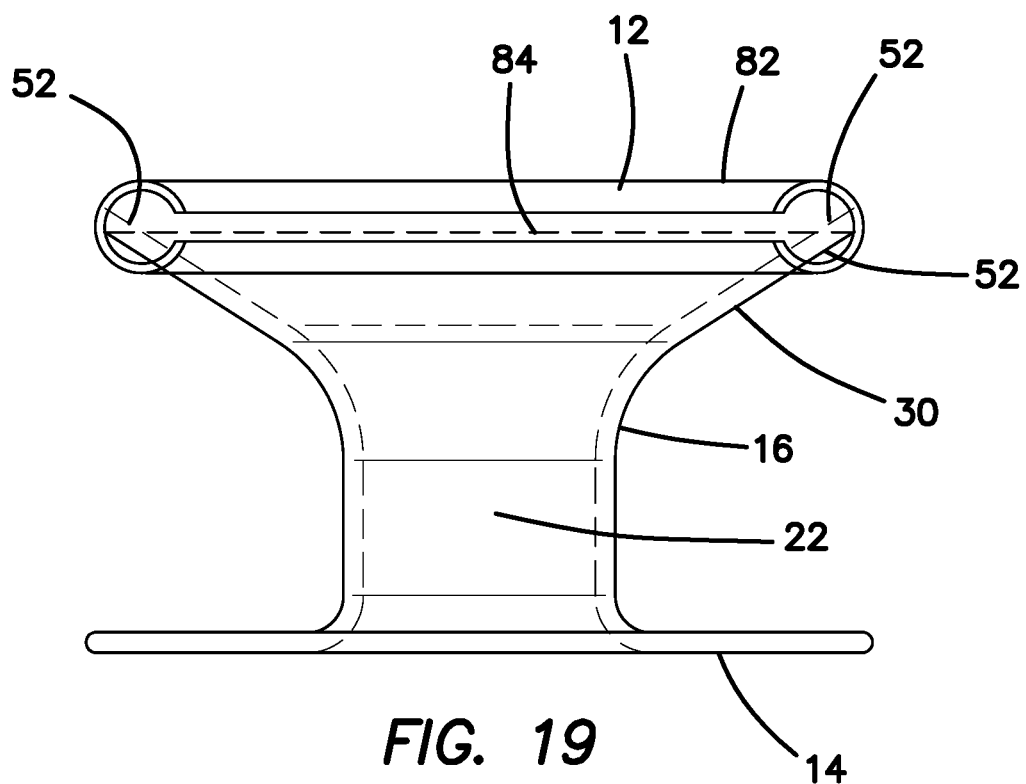
FIG. 19 is a cross-sectional side view of mesh guard with an extruded proximal ring according to the present invention.
Figure 20:
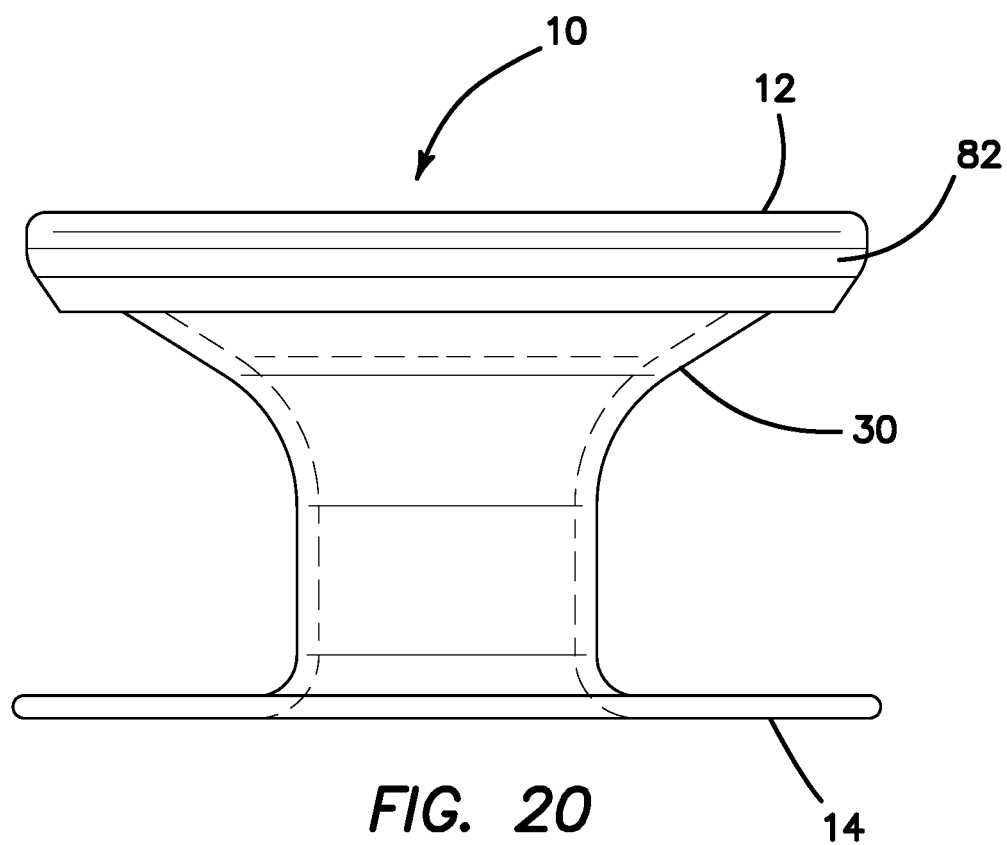
FIG. 20 is a side view of a mesh guard with an over-molded ring according to the present invention.
Figure 21:
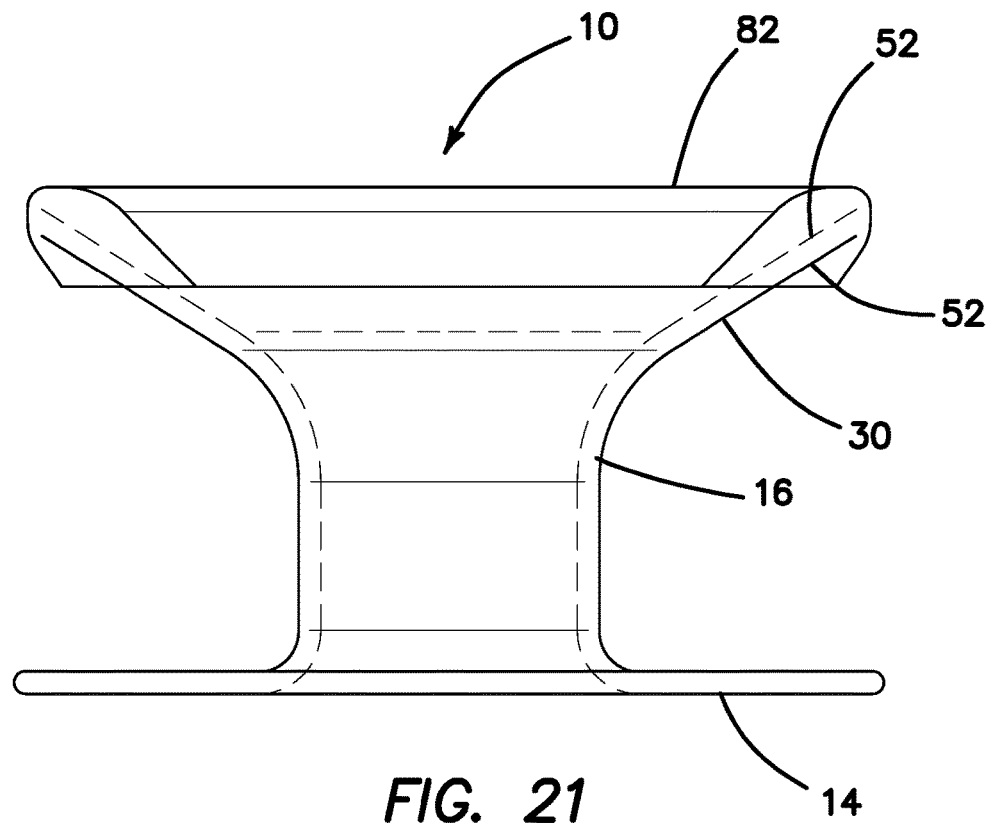
FIG. 21 is a cross-sectional side view of a mesh guard with an over-molded ring according to the present invention.

Turning now to FIGS. 18-19, there is shown another variation of a ring 82 connected to the proximal end of the mesh guard 10. In this variation, the ring 82 is an extruded ring 82. The ring 82 is attached to the top flange 30 at the proximal end 12. The ring 82 is sized and configured to circumferentially encompass the proximal end 12 to cover and contain the free ends of the filaments 52 of the mesh sleeve and to prevent fraying of the loose filament ends. The ring 82 is made of polymeric material and may be rigid or flexible. The ring 82 has a smooth outer surface and a channel 84 formed by the inner surface of the ring 82. The ring 82 is formed by extrusion. Adhesive or sealant is placed inside the channel 84 of the ring 82. The proximal end 12 of the mesh guard 10 including any free filament ends, frayed or loose filaments 52 are tucked into the channel 84 of the ring 82. The adhesive is allowed to cure and the ring 82 remains attached to the mesh guard 10. The ring 82 not only captures and contains the filaments 52 at their free end, but also, the ring 82 provides added rigidity and protection at the proximal end 12.

Figure 22:
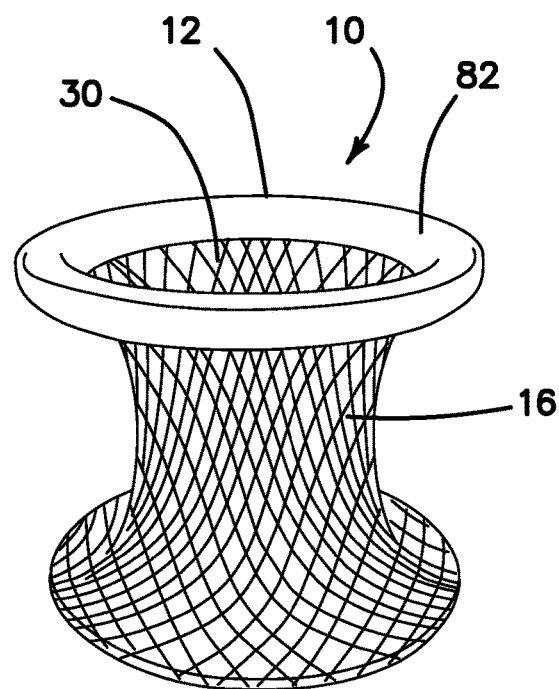
FIG. 22 is a top perspective of a mesh guard with an over-molded ring according to the present invention.
Figure 23:
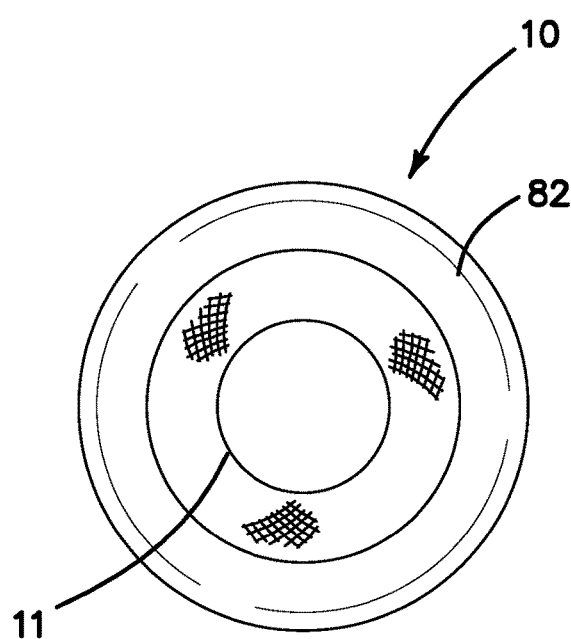
FIG. 23 is a top view of a mesh guard with an over-molded ring according to the present invention.
Figure 24:
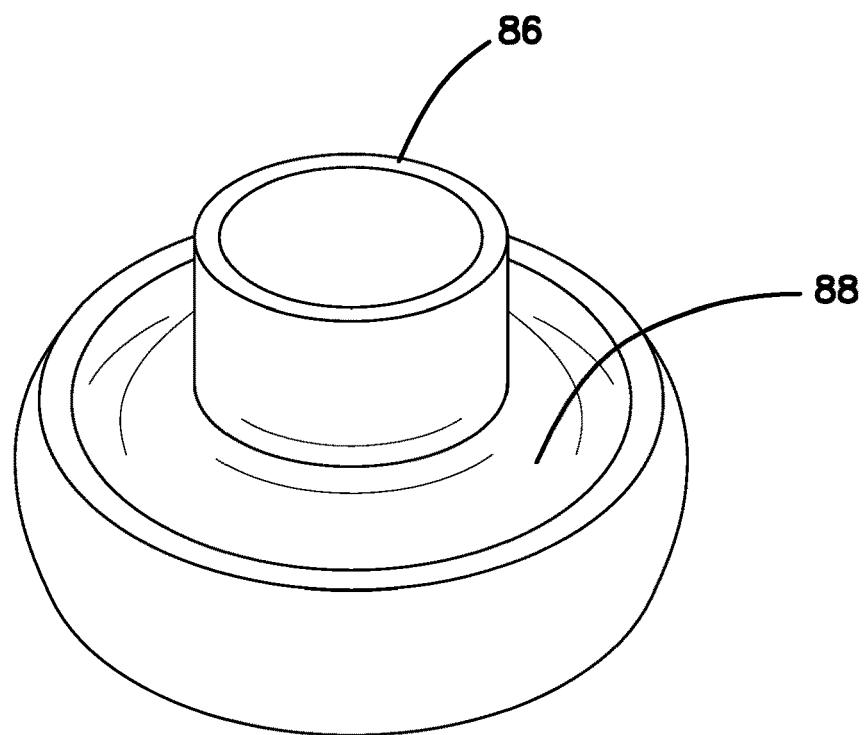
FIG. 24 is a top perspective view of a casting dish for forming an over-molded ring according to the present invention.

Turning now to FIGS. 20-24, there is shown another variation of a ring 82 connected to the proximal end 12 of the mesh guard 10. In this variation, the ring 82 is molded over the proximal end 12. The ring 82 is molded to the top flange 30 at the proximal end 12. The ring 82 encompasses the proximal end 12 to cover and contain the free ends of the filaments 52 of the mesh sleeve and to prevent fraying of the loose filament ends. The ring 82 is made of silicone such as room temperature vulcanization silicone or other polymeric material and may be rigid or flexible. A mold such as a casting dish 84 shown in FIG. 23 is created. The casting dish 84 includes an annular reservoir 88 that is sized and configured to receive the proximal end 12 of the mesh guard 10. Casting material is poured into the reservoir 88 and the proximal end 12 of the mesh guard 10 is inserted into the reservoir 88. The casting material is allowed to cure and the mesh guard 10 is carefully removed from the casting dish 86. The ring 82 not only captures and contains the filaments 52 at their free end, but also, the ring 82 provides added rigidity and protection at the proximal end 12. The resulting mesh guard 10 with the over molded ring 82 is shown in FIGS. 22-23.

Figure 25:
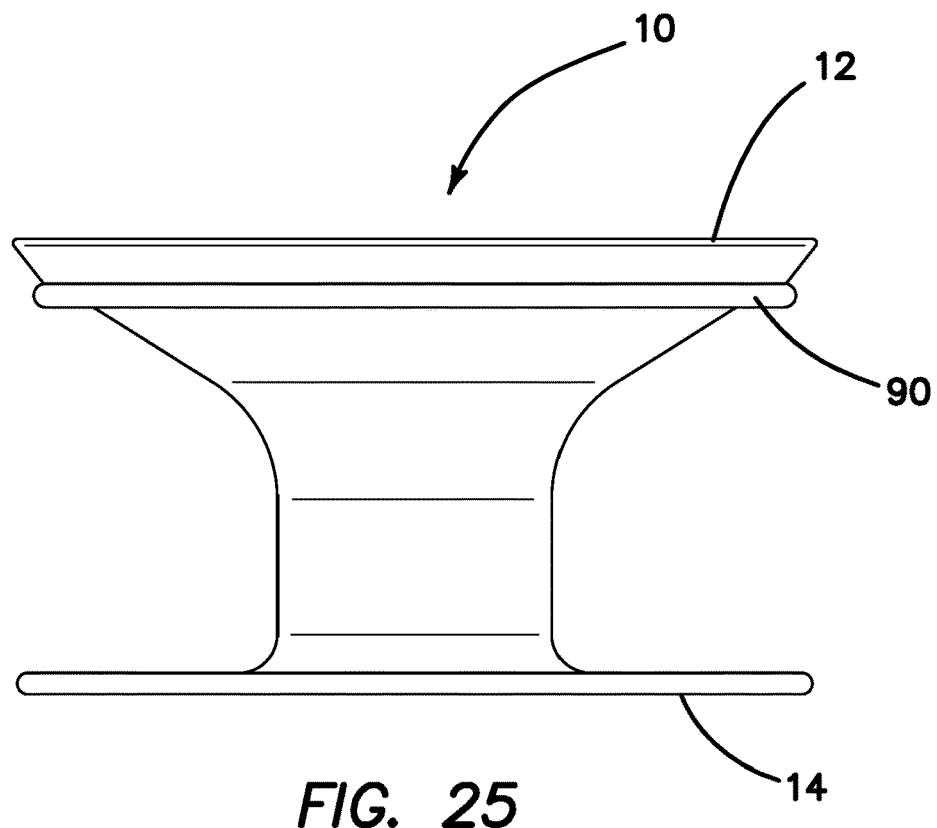
FIG. 25 is a side view of a mesh guard with a proximal bead ring according to the present invention.
Figure 26:
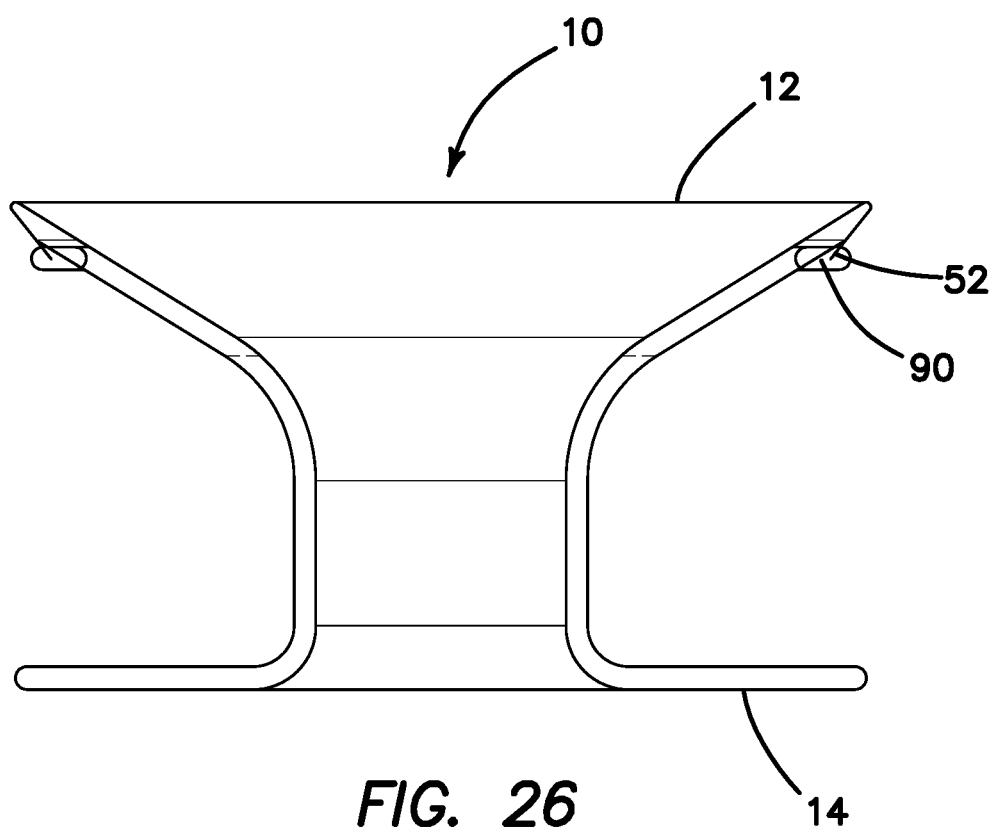
FIG. 26 is a cross-sectional side view of a mesh guard with a bead ring according to the present invention.

Turning now to FIGS. 25-26, there is shown another variation of covering the frayed filaments 52 at the proximal end 12 of the guard 10 includes laying a bead 90 of sealant or caulking. The bead 90 of sealant is placed along the frayed edges of the mesh and excess sealant is carefully removed. Care is taken to ensure that the frayed edges are completely concealed. The sealant is allowed to cure to form the rigid or flexible bead 90. The bead 90 not only captures and contains the filaments 52 at their free end, but also, the bead 90 provides added rigidity and protection at the proximal end 12.

Figure 27:
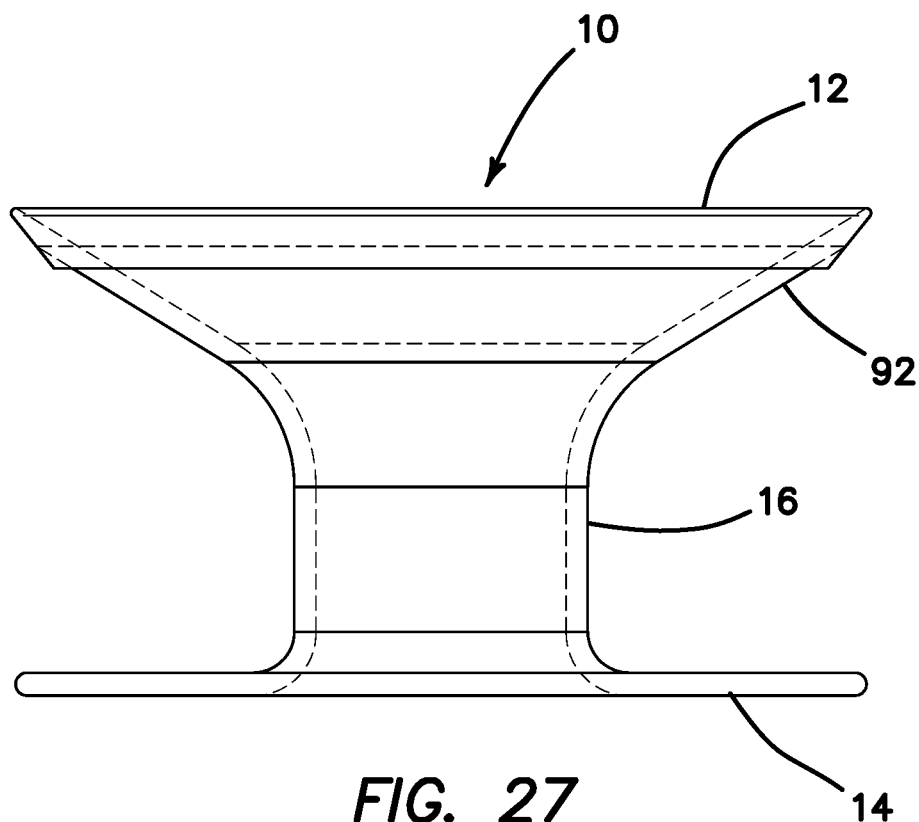
FIG. 27 is a side view of a mesh guard with a heat sealed proximal ring according to the present invention.
Figure 28:
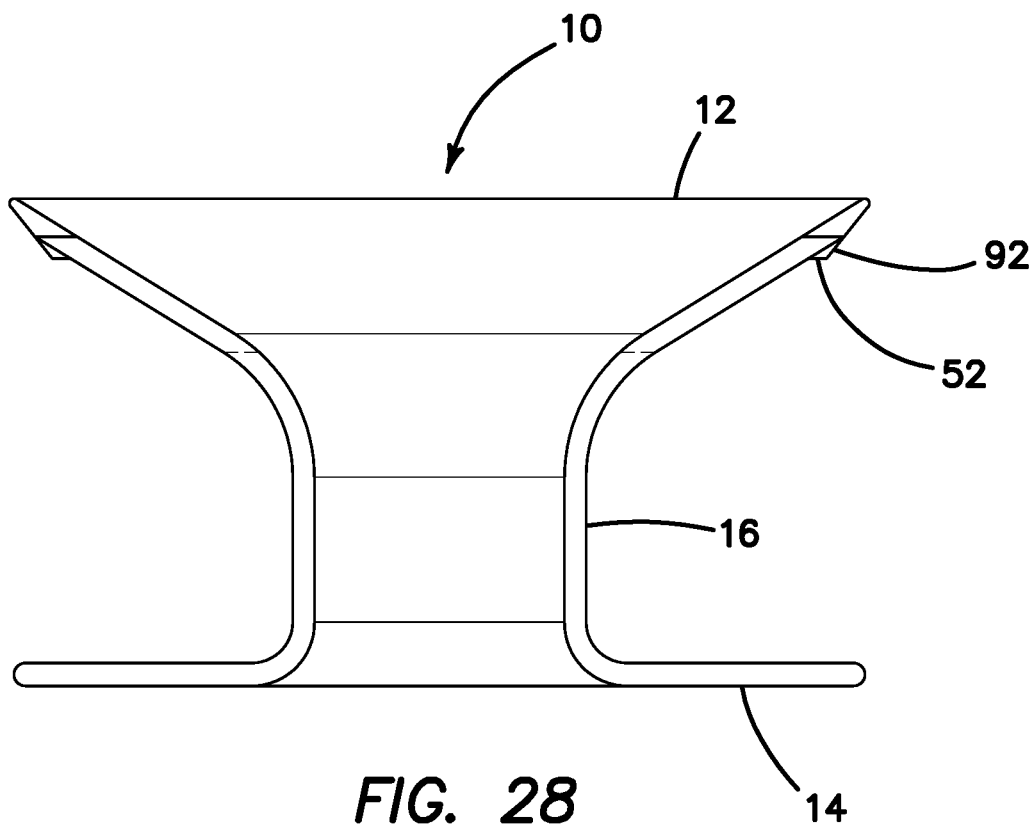
FIG. 28 is a cross-sectional side view of a mesh guard with a heat sealed proximal ring according to the present invention.

Turning now to FIGS. 27-28, there is shown another variation of covering the frayed filaments 52 at the proximal end 12 of the guard 10 includes heat sealing. In this variation, no extra materials are needed conceal the frayed edges. The excess distal ends of the filaments 52 are trimmed using a hot tool such as a soldering iron, hot wire or hot knife. The heat melts and seals the ends of the mesh together to prevent further fraying of the filaments. The process results in a small band 92 of hot sealed filaments 52. The heat sealed band 92 not only seals and contains the filaments 52 at their free end, but also, the band 92 provides added rigidity and protection at the proximal end 12. Although FIGS. 15-23 describe a ring 82 and FIGS. 25-28 describe a bead 90 at the proximal end 12 of the guard 10, the invention is not so limited and a ring 82 can be formed at the proximal end 12 and/or the distal end 14 of the guard 10 and a bead 90 can be formed at the proximal end 12 and/or the distal end 14 of the guard 10.

Figure 30:
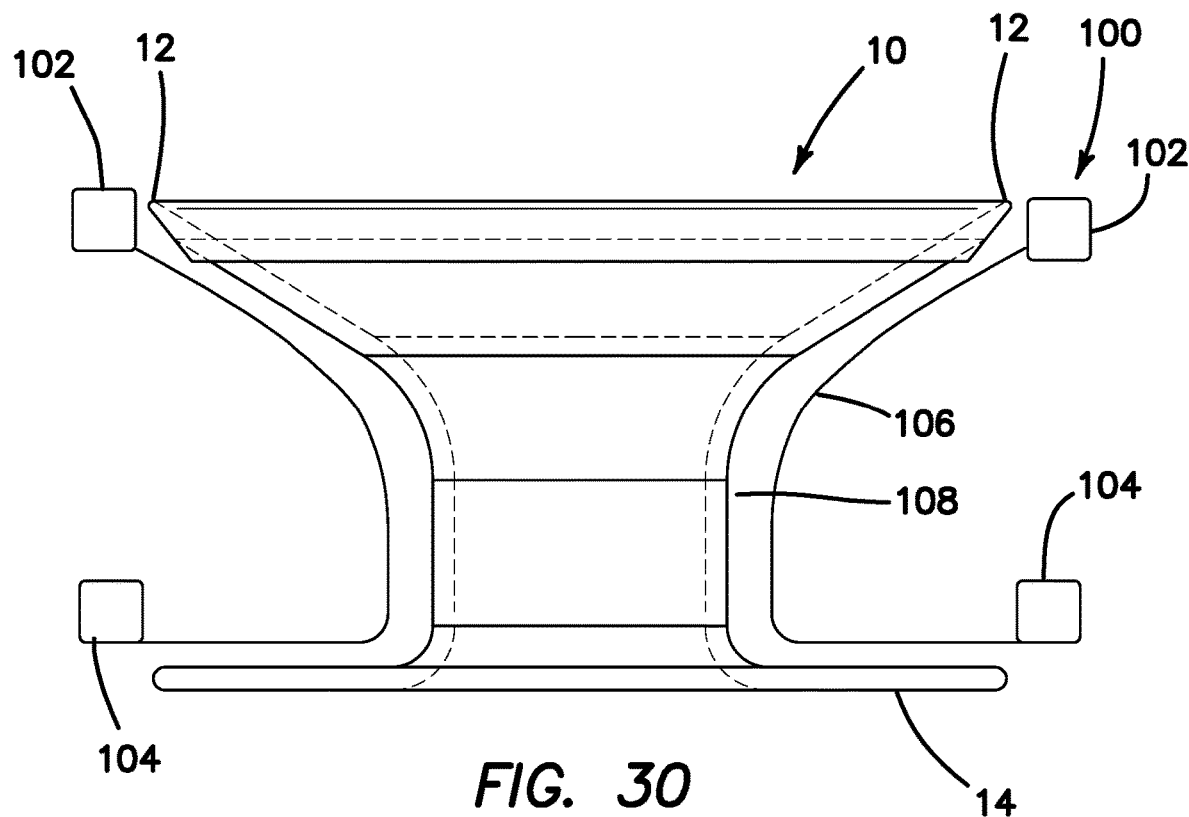
FIG. 30 is a side elevational, sectional view of a guard and retractor according to the present invention.
Figure 31:
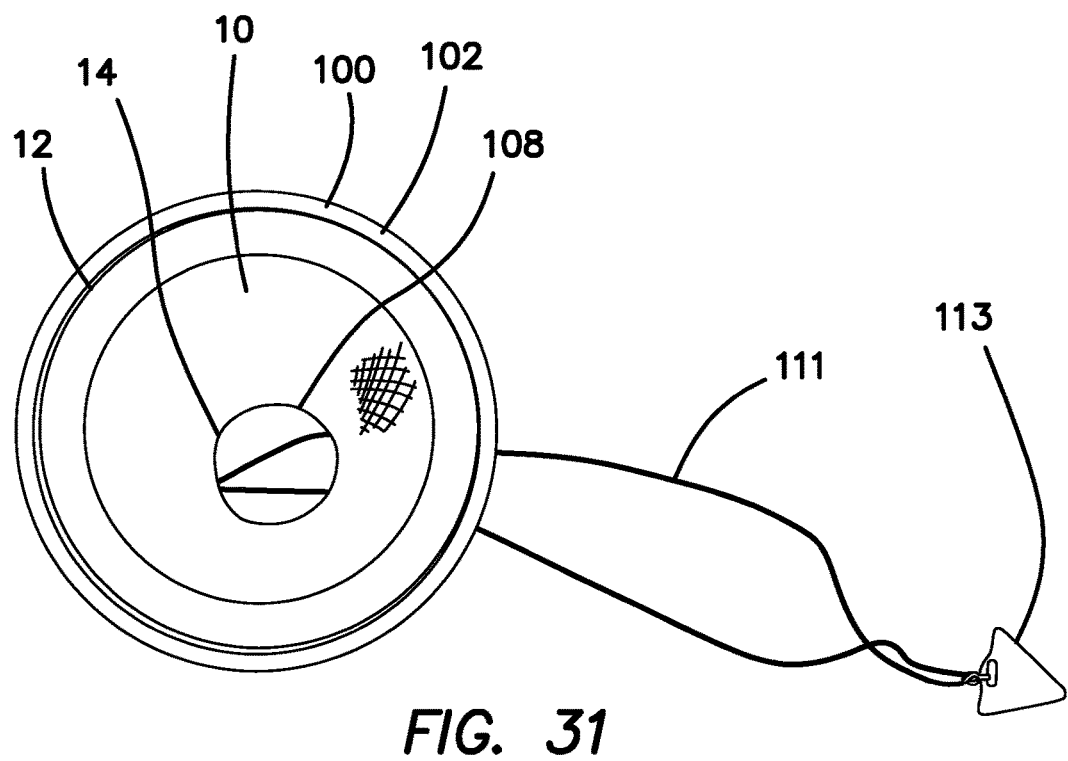
FIG. 31 is a top view of a guard and retractor according to the present invention.

Turning now to FIGS. 30-31, there is shown a system comprising a retractor 100 and guard 10. The retractor 100 includes a first ring 102 and a second ring 104 interconnected by a flexible sidewall 106. The tubular sidewall 106 defines a central opening 108 extending along the longitudinal axis of the retractor 100. The second ring 104 is resilient and compressible. The second ring 104 can be compressed and inserted into an incision or body orifice where it expands to create a securement. For example, when inserted through an incision in the abdomen, the second ring 104 is compressed to pass through the incision and allowed to expand against the abdominal wall inside the abdominal cavity. When inserted into a vaginal canal, for example, the second ring 104 is compressed and then allowed to expand to create a securement against the vagina. The first ring 102 resides above the abdominal wall or proximally outside the patient. If inserted into the vaginal canal, the first ring 102 of the retractor 100 resides above the entrance to the vagina outside the patient. The first ring 102 is configured such that it can be rolled down to retract and enlarge the opening in the abdominal wall or other incision or to retract and enlarge the vaginal canal or other orifice while the second ring 104 remains anchored in an expanded state inside the patient. The first and second rings 102, 104 have approximately the same diameter. In another variation, a larger first ring 102 relative to the second ring 104 allows for more space to work and cut tissue against. The sidewall 106 can be made of a polymer polyurethane laminate or similar flexible material and, in one variation, including woven material to resist cutting through the sidewall 106. The first ring 102 is configured to be rolled/flipped over itself to wrap the sidewall 106 around the first ring 102, shortening the length of the sidewall 106 between the rings 102, 104. This action pulls the second ring 104 of the retractor 100 closer to the first ring 102 and the sidewall 106 into a taut relation between the rings 102, 104 so as to retract tissue located between the two rings 102, 104. In use, for example, the retractor 100 is inserted prior to insertion of the guard 100 into the cavity or orifice. The second ring 104 of the retractor 100 is compressed for easy insertion into the orifice/incision and then allowed to expand into an open configuration inside the patient. The first ring 102 of the retractor 100 that is resident outside the body is rolled about itself to roll the sidewall 106 of the retractor 100 onto the first ring 102. This action retracts tissue at the margin to create a wide open working channel for the surgeon to operate. The guard 10 is then inserted into the central lumen of the retractor 100. The distal end 14 of the guard 10 may be scrunched down and reduced in width into a compact configuration during insertion and then allowed to expand to self-anchor into position. The proximal end 12 of the guard 10 is located within the first ring 102 of the retractor 100 as shown in FIGS. 30-31. The diameter of the proximal end 12 of the guard 10 is approximately equal to or less than the inner diameter of the first ring 102 of the retractor 100 in the relaxed state as shown in FIGS. 30-31. The surgical procedure such as morcellation may then be carried out with the working channel protected by the guard 10. The guard 10 advantageously protects the surrounding tissue as well as the retractor 100 from any sharp blade used in the surgical procedure helping to maintain the integrity and preventing inadvertent contamination of the surgical site while providing the surgeon with a mechanism to perform morcellation safely and quickly.

Figure 32:
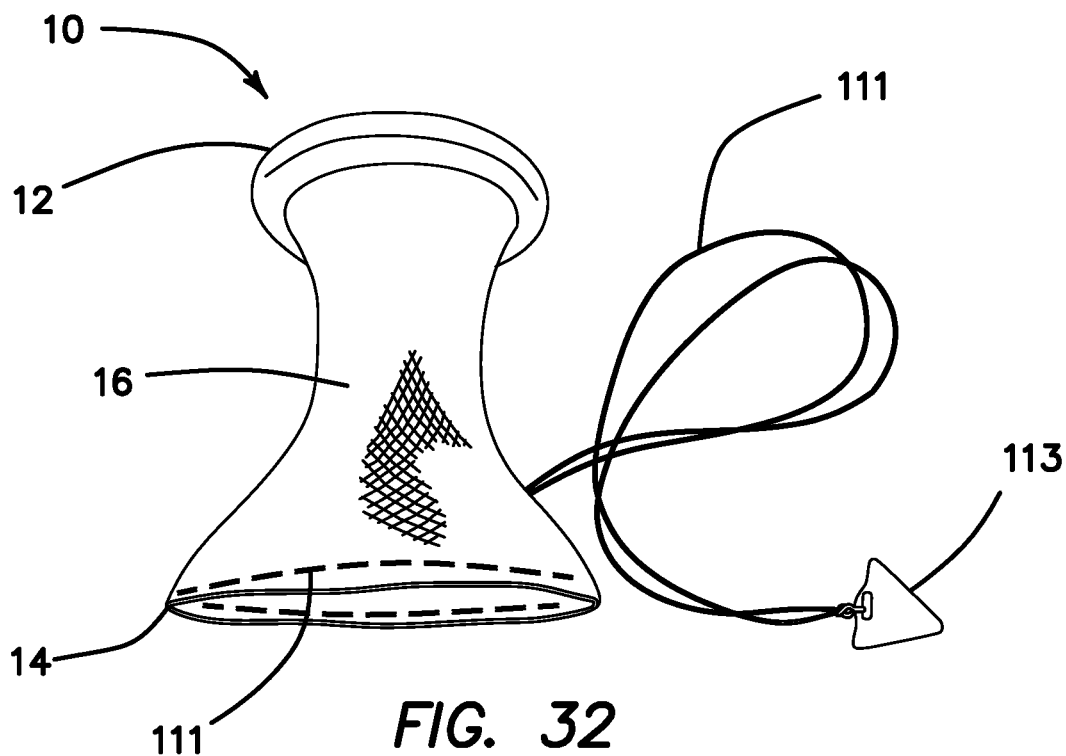
FIG. 32 is a bottom perspective view of a guard with tether according to the present invention.
Figure 33:
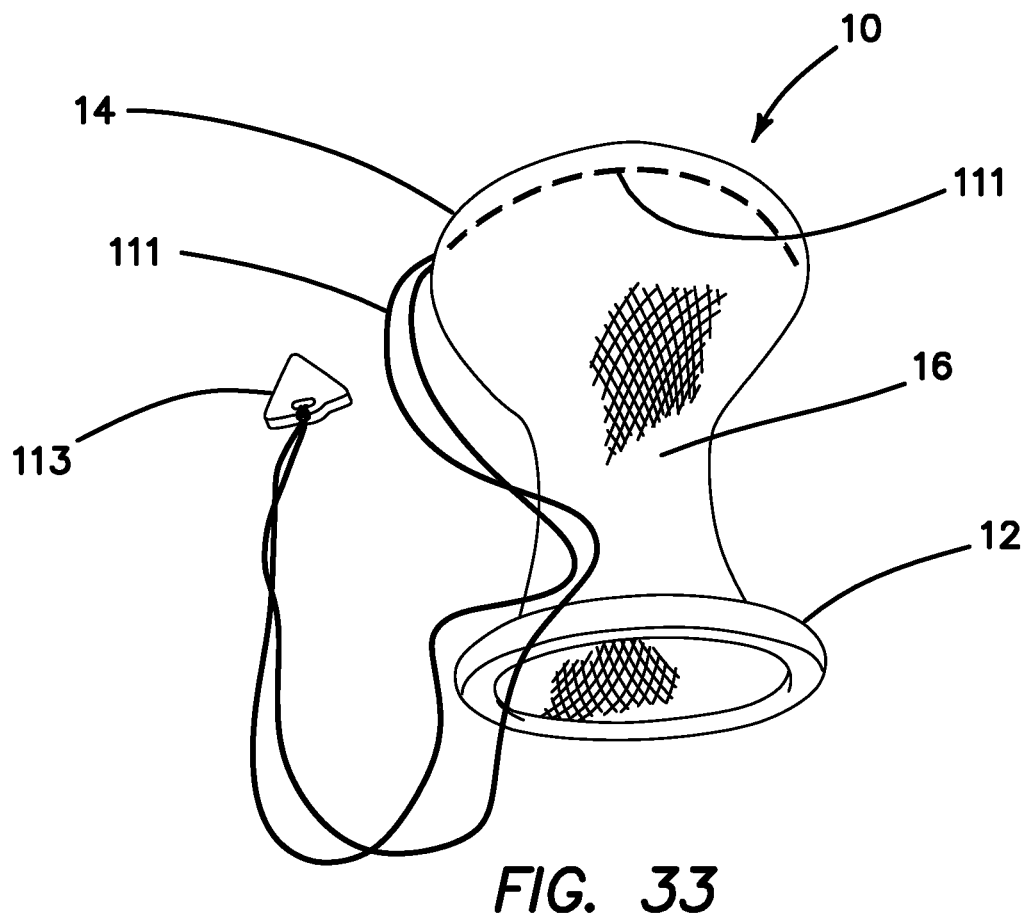
FIG. 33 is a top perspective view of a guard with tether according to the present invention.
Figure 34:
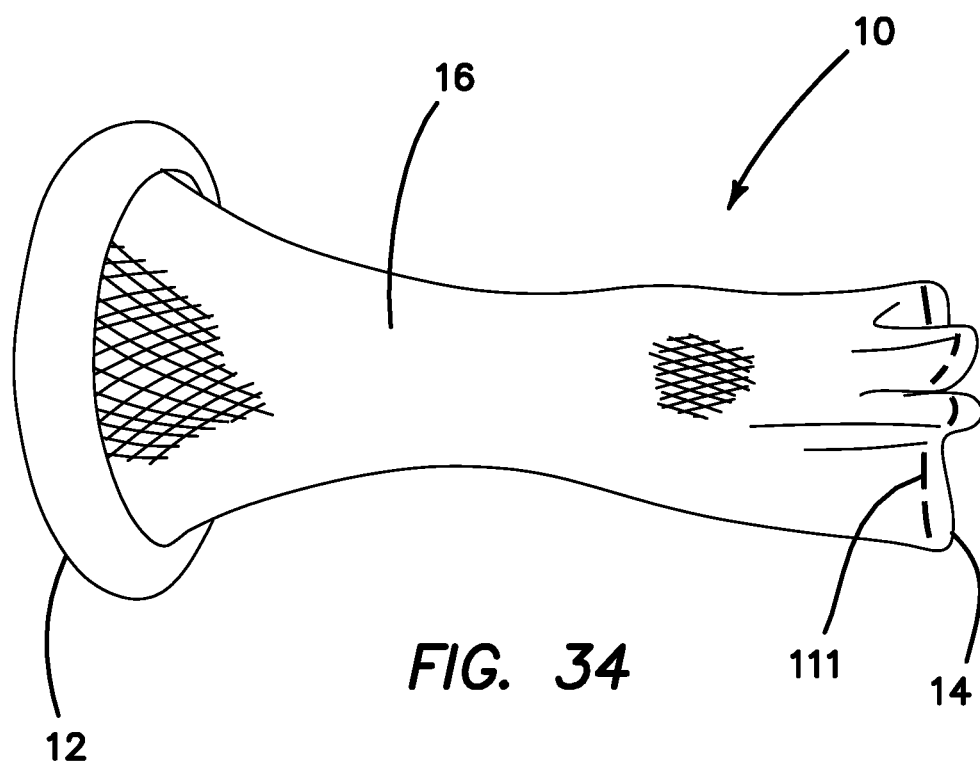
FIG. 34 is a bottom perspective view of a guard with tether according to the present invention.

Turning now to FIGS. 32-34, there is shown another variation of the guard 10 that includes a drawstring tether 111. The tether 111 is a polyester filament or other string or pull-wire that is weaved around the distal end 14 of the guard 10. The tether 111 is connected to the distal end 14 such that it is movable with respect to mesh sidewall 16 in drawstring fashion when pulled to cinch and reduce the lateral width of the distal end 14 of the guard 10 into a reduced configuration shown in FIG. 34 relative to the expanded configuration shown in FIGS. 32 and 33. In one variation, the tether 111 is weaved in and out of the windows 50 of the mesh sidewall 16 as is clearly visible in FIG. 32. The tether 111 is connected to a tag 113 at one end. When pulled at the tag 113, the width of the distal end 14 will be moved to a reduced configuration that is facilitates insertion and removal of the guard 10. When the tag 113 is released, the heat-set distal end 14 will tend to return to its normal width into an expanded or relaxed configuration shown in FIGS. 32 and 33. When being inserted into the patient, care is taken to keep the tether 111 outside of the central lumen 22. If a system in which a retractor 100 and guard are employed together, the tether 111 is located between the retractor sidewall 106 and the sidewall 16 of the guard 10 and along the longitudinal axis of the guard 10 such that the tag 113 is resident outside the patient. Upon removal of the guard 10, the spring-back feature of the distal end 14 that is biased to return to its heat set expanded configuration may hamper removal of the device and even splash any bodily fluid when removed from the patient. The tether 111 advantageously alleviates these removal problems. During the surgical procedure, the tag 113 remains outside the body. When it is time to remove the guard 10 from the patient, the tether 111 is first pulled and held while the guard 10 is removed from the patient. Once the guard 10 is extracted the tether 111 can be released carefully to return the distal end 14 to it expanded configuration. The tether 111 advantageously aids the insertion and removal of the guard 10.

Figure 35:
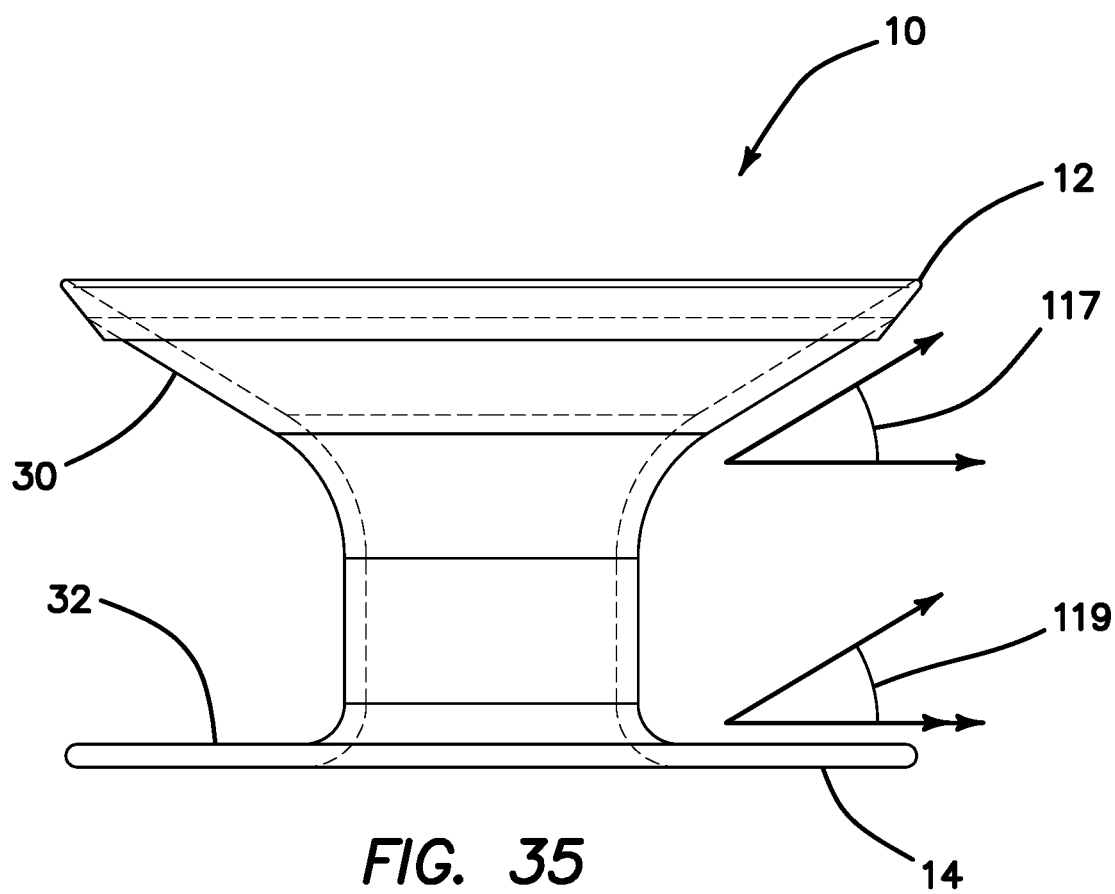
FIG. 35 is a side elevational view of a guard according to the present invention.

Turning now to FIG. 35, there is shown a side elevational view of a guard 10 according to the present invention. The guard 10 includes a top flange 30 and a bottom flange 32 that extend outwardly away from the longitudinal axis. The longitudinal axis is normal to a plane. The top flange 30 is angled circumferentially with respect to this plane at an angle 117. Angle 117 is approximately 45 degrees with respect to the plane normal to the longitudinal axis. An angle 117 greater than 45 degrees generally results in the top flange 30 losing its retention abilities and would tend to slide down into the orifice and generally create a longer working channel. An angle 117 less than 45 degrees would result in reduced visualization and space for contained, protected morcellation. The bottom flange 32 is angled circumferentially with respect to a plane normal to the longitudinal axis at an angle 119. Angle 119 is approximately 0 to 45 degrees with respect to the plane normal to the longitudinal axis. This range for angle 119 allows for maximum bottom flange 32 retention inside the body preventing the guard 10 from easily being pulled proximally out of the body. An angle 119 that is much greater than 45 degrees would reduce surface area contact between the bottom flange 32 and the area inside the body, thereby, reducing retention abilities. A negative angle 119 would result in the bottom flange 32 losing its retention abilities and cause the guard 10 to slip outside the body. In another variation, the guard 10 is provided with inflatable fixation at the distal end 14 such as an inflatable balloon located circumferentially around the distal end 14 of the guard 10 and having an inflation pathway extending toward the proximal end 12.

The mesh guard 10 is composed of a single piece of mesh formed to fit vaginally or abdominally. The device is intended to aid surgeons during procedures that require tissue morcellation. During procedures that require tissue morcellation, surgeons risk accidentally cutting marginal tissue and organs other than the targeted tissue as well as damaging containment bags and/or retractors used in conjunction with the morcellation procedure. The guard 10 provides needed protection and advantageously provides 360 degrees of protection around the working channel, central lumen 22 against scalpels and sharp instruments. For vaginal use, such as during a hysterectomy, the uterus is detached. A retractor is inserted vaginally and anchored securely with respect to the body orifice. Clamps are used to grasp the bottom flange 32 of the mesh guard 10. In grasping the bottom flange 32 the flared distal end 14 is reduced in its lateral dimension such as shown in FIG. 6. The mesh guard 10 with reduced distal end is inserted into the vagina. The bottom flange 32 is released. Upon release of the distal end 14, the mesh guard 10 tends to spring back towards it nominal resting configuration. In doing so, the bottom flange 32 expands laterally to anchor the mesh guard 10 with respect to the anatomy with the distal end 14 and bottom flange 32 of the mesh guard 10 residing inside the patient, the midsection 40 of the guard 10 traversing the vagina and the top flange 30 residing outside the patient and resting above the body opening and visible outside vagina. The surgeon may check to see if the guard 10 is anchored properly by adjusting and pulling on the guard 10 or adjusting the bottom flange 32. The vaginal hysterectomy is continued. The detached uterus is grasped with graspers and pulled though the central lumen 22 of the guard 10 until at least a portion of the tissue is visible from outside the vagina. The surgeon will then use a scalpel to cut into the detached uterus such that a smaller portion of it can be pulled out through the guard 10. The surgeon will repeat this cutting process until the entire uterus is removed or reduced in sized sufficient for extraction. The guard 10 advantageously provides protection for the cutting process, giving the surgeon confidence to perform the surgery quickly and easily. A containment bag may also be employed with the tissue guard 10. A containment bag is deployed inside the patient and the detached uterus is placed inside the bag. The uterus is too large to be removed and must be morcellated for removal. The mouth of the bag is pulled to the surface through the vaginal canal and through the retractor if one is in position at the orifice. The mesh guard 10 according to the present invention is inserted into the mouth of the bag and anchored with respect to the orifice. Alternatively, the bag may be placed first and followed by a retractor. In such a case, the guard 10 is placed into the working channel of the retractor to protect both the bag and the retractor.

The mesh guard 10 may also be used abdominally. An incision is made through the abdominal wall to access the abdominal cavity, such as during a hysterectomy, in which the uterus is detached. A retractor is inserted into the incision and anchored securely with respect to the incision. Clamps are used to grasp the bottom flange 32 of the mesh guard 10. In grasping the bottom flange 32 the flared distal end 14 is reduced in its lateral dimension such as shown in FIG. 6. The mesh guard 10 with reduced distal end is inserted into the abdominal cavity. The bottom flange 32 is released. Upon release of the distal end 14, the mesh guard 10 tends to spring back towards it nominal resting configuration. In doing so, the bottom flange 32 expands laterally to anchor the mesh guard 10 with respect to the anatomy with the distal end 14 and bottom flange 32 of the mesh guard 10 residing inside the patient, the midsection 40 of the guard 10 traversing the incision site and the top flange 30 residing outside the patient and resting atop the abdominal wall. The surgeon may check to see if the guard 10 is anchored properly by adjusting and pulling on the guard 10 or adjusting the bottom flange 32 as needed. The vaginal hysterectomy is continued. The detached uterus is grasped with graspers and pulled though the central lumen 22 of the guard 10 until at least a portion of the tissue is visible from outside the patient. The surgeon will then use a scalpel to cut into the detached tissue such that a smaller portion of it can be pulled out through the guard 10. The surgeon will repeat this cutting process until the entire uterus is removed or reduced in sized sufficient for extraction. The guard 10 advantageously provides a protection for the cutting process, giving the surgeon confidence to perform the surgery quickly and easily. A containment bag may also be employed with the tissue guard 10. A containment bag is deployed inside the patient and the detached tissue specimen such as the uterus is placed inside the bag. The uterus is too large to be removed and must be morcellated for removal. The mouth of the bag is pulled to the surface through the abdominal incision and through the retractor if one is in position across the incision site. The mesh guard 10 according to the present invention is inserted into the mouth of the bag and anchored with respect to the orifice. Alternatively, the bag may be placed first and followed by a retractor being placed inside the mouth of the bag. In such a case, the guard 10 is placed into the working channel of the retractor to protect both the bag and the retractor. Although the guard was described for use in a hysterectomy, it can be used for other medical procedures as well, including but not limited to procedures that involve the extraction of target tissue.

The bottom flange 32 functions as a retention flange that anchors the guard 10 into the body. The bottom flange is also able to adjust to how long or short the patient's vaginal canal is or to how thick the patient's abdominal wall is. The flange shape and material allows the mesh to shift and stretch and advantageously increase in channel length and conform to the anatomy in which it is placed. Also, the dual mesh layers provide a thick surface to prevent sharp instruments from cutting through. The mesh guard may be used at any point during a surgical procedure when a cutting surface or protection against sharp objects is needed. Using the guard with a retractor is optional when performing a procedure. The guard may also be selectively coated with a polymer material, meaning that only part of the guard such as the top flange is coated with a polymer solution and the bottom flange is left uncoated in order to provide more flexibility at the distal end 14 when adjusting to a patient's anatomy. Of course, the guard may be scaled appropriately and proportionally in size to fit in different body openings.

Figure 29:
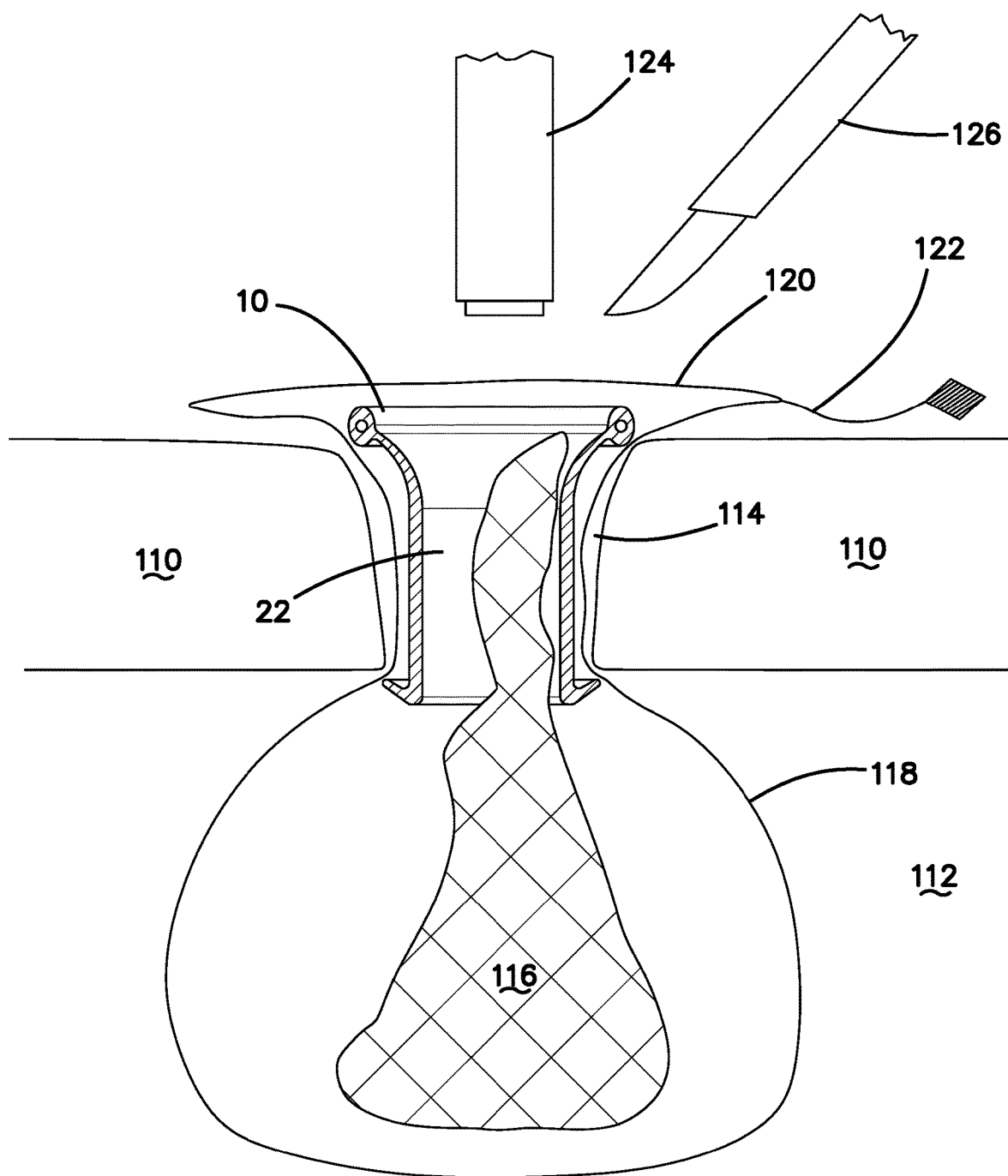
FIG. 29 is a cross-sectional view of a containment bag and guard placed in an opening in a body wall according to the present invention.

Turning now to FIG. 29, there is shown an exemplary closed morcellation procedure according to the present invention. A small incision is made in a patient in the location of an abdominal wall 110 and a body cavity 112 is accessed through an opening 114 across the abdominal wall 110. Opening 114 in FIG. 29 may also be representative of a vaginal canal and the abdominal wall 110 representative of the tissue margin. Laparoscopic techniques and instruments such as trocars, laparoscopes, graspers and scalpels may be employed to create the single site opening, spy the targeted tissue and detach the targeted tissue from surrounding tissue structures. Additional incisions or access sites may be employed to insert instruments and scopes to facilitate the procedure. After the targeted tissue 116 such as at least a part of the uterus in a hysterectomy procedure is completely detached, a specimen retrieval bag 118 is inserted through the opening 114 in the wall 110 and placed inside the body cavity 112. The bag 118 may be delivered through a trocar or cannula that is placed across the wall 110 or inside the vagina. The bag 118 is unfurled and oriented inside the body cavity 112. The targeted tissue 116 is placed into the bag 118 through an opening 120 in the bag 118. Various types of bags 118 may be employed. The bag 118 may be transparent such that the contents may be observable from outside the bag 118 via a scope placed into the body cavity 112 through a secondary incision site across the abdominal wall 110. The contents of the bag 118 may be illuminated from outside the bag 118. The location of the targeted tissue 116 may also be observed through a transparent bag 118 to ascertain the progress of morcellation as well as the position and proximity of the targeted tissue 116 relative to the opening 114. Also, the bag 118 is observed via a secondary site insertion to ascertain the state of the bag 118 making sure that it is not tangled and twisted and that the specimen is moved toward the opening without pulling the bag 118 along with it which may result in the bag being accidentally coming into contact with a blade and being severed. An opaque bag 118 may also be employed. The material of the bag 118 is also important. Generally, made of plastic, the bag is strong enough to withstand pulls and tugs, has sufficient stretch properties and is relatively thin, flexible and resilient to puncture and tears. The bag is folded and reduced in size such that it can be inserted through the small incision/trocar of approximately at least 5 mm in diameter. Also, when opened, the bag is large enough to receive a large piece of tissue, extend through the opening 114 to the surface of the abdominal wall 110 and create a sufficiently large working space inside the bag 118 for instruments, scopes, morcellators 124, and scalpels 126 as shown in FIG. 29. The bag 118 includes a tether or drawing string 122 configured to cinch the opening closed and to open the bag 118. The bag 118 withstands insufflation pressures and does not leak.

After the targeted tissue 116 is placed inside the bag 118, the tether 122 is grasped by hand or with a laparoscopic grasper and at least a portion of the bag 118 is pulled through the abdominal wall opening 114. Pulling the tether 122 closes the bag opening 120. The initial incision may be increased to approximately 15-40 mm prior to pulling the bag 118 through the opening 114. If the targeted tissue 116 is too large to fit through the opening 114, the targeted tissue 116 will sit inside the body cavity 112 below the abdominal wall 10. The remainder of the bag 118 including the opening 120 of the bag 118 will be pulled through the abdominal wall opening 114 and extend through the opening 114 to outside the patient and along the upper surface of the abdominal wall 110 as shown in FIG. 29. The bag 118 may be rolled down and/or pulled taut across the surface of the abdominal wall 110 to maintain its position and provide some tissue retraction at the opening 114.

A guard 10, according to the present invention, is inserted in through the opening 120 of the bag 118. Once the guard 10 is placed, the surgeon will grasp the specimen 116 and pull it up through the central lumen 22 as far as possible. The surgeon will then begin morcellating the specimen 116 with a scalpel 126, cutting the specimen 116 to reduce its size. Ideally, the surgeon will "core" or "peel" the specimen 116 to keep it in one piece as much as possible. However, more likely than not, the specimen 116 will be reduced in multiple pieces. While morcellating through the incision, the surgeon may maintain pneumoperitoneum in the abdominal cavity 112 so that the progress of the morcellation can be observed laparoscopically through a lateral port placed at a secondary site into the cavity 112. Once the specimen 116 is morcellated, crushed, reduced enough to pull the remaining portion through the incision, the guard 10 is removed, and the bag 118 and its contents that may include the pieces created during morcellation, are pulled out of the patient. The bag 118 will prevent the remaining small pieces from being left in the abdominal cavity 112, thereby, maintaining the closed system; whereas in a traditional morcellation, the surgeon must go back and painstakingly search and collect the pieces scattered amid the pelvic cavity to prevent potentially seeding new tumor sites. The surgeon may choose to take a final look at the patient laparoscopically and then close the wounds. While described for an abdominal removal and morcellation, the above-described procedure can be performed via the vagina orifice as well if the cervix has been removed. Following the same process, the bag 118 will be introduced and the specimen 116 placed into the bag 118 laparoscopically. Rather than pull the tether 122 through the abdominal wall opening 114, it would be pulled through the vagina. The surgeon may roll the bag 118 down or pull it taut to maintain its position and provide some retraction. The surgeon would place the guard 10 vaginally to protect integrity of bag 118, protect the tissue margin and to maintain a closed system, grasp the specimen 116 to bring it out, and morcellate to reduce the size of the specimen 116. Morcellation of the specimen is performed in the location of the guard 10 and/or against the guard 10 surface protecting the surrounding tissue and bag from inadvertent incisions. The surgeon may maintain pneumoperitoneum and watch the progress of the morcellation laparoscopically. Once the specimen 116 is morcellated, crushed, reduced enough to pull the remaining portion through the vagina, the guard 10 is removed, and the bag 118 and its contents, including the pieces created during morcellation, are pulled out of the patient. The bag 118 will prevent the remaining small pieces from being left in the abdominal cavity preventing harmful material such as cancerous cells form being disseminated in the abdominal cavity, maintaining the closed system; whereas in a traditional morcellation, the surgeon must go back and painstakingly search and collect the pieces scattered amid the pelvic cavity search for the pieces amid the pelvic cavity. The surgeon may choose to take a final look at the patient laparoscopically and will close the vaginal cuff and abdominal incisions.

A retractor having a central lumen may also be employed and placed inside the mouth of the bag 118 to retract tissue along with the bag enlarging the opening. Then, the tissue is morcellated with the bag in place. A mesh guard 10 as previously described is provided and used in conjunction with the bag 118 and the retractor. The guard 10 is placed inside the central lumen of the retractor with the retractor being located between the guard 10 and the bag 1. Of course, the guard 10 may be used without the retractor. If a retractor is not used, the guard is placed into the mouth 120 of the bag 118 in the location of the incision/vaginal canal. The guard is inserted into the mouth 120 of the containment bag 118 after the bag 118 is placed inside the patient and pulled through the incision/vaginal canal. The guard 10 protects the plastic bag 118 and adjacent tissue at the margin from being inadvertently cut by the blade used by the surgeon to morcellate the target tissue. The guard 10 may also serve as a cutting board against which a surgeon may cut the target tissue if needed.

If a retractor is used inside the bag 118, the retractor advantageously not only retracts the tissue but also retracts part of the bag, keeping the bag out of the way of a morcellating blade and, thereby, protecting the bag from cuts and punctures. A typical retractor includes a top ring and bottom ring with a flexible sidewall connected therebetween. The bottom ring is inserted through the incision and resides inside the patient whereas the top ring of the retractor resides above the patient. The top ring is rolled/flipped over itself like the bag to pull the lower ring of the retractor closer and the sidewall into a taut relation between the rings. The lower ring of the retractor advantageously retracts the portion of the bag 118 inside the patent and away from potential damage arising from punctures and tears from the blade.

The tissue is morcellated in a fashion desired by the surgeon. Generally, a small part of the target tissue is pulled to the outside of the patient while the larger portion of the target tissue remains inside the patient. The surgeon will take a blade and make a circumferential cut of approximately 180 degrees or 360 degrees around the circumference of the protruding tissue without severing the protruding tissue from the remainder of the target tissue. Keeping the protruding tissue intact with the larger piece inside the patient permits the surgeon to continue to grasp the tissue without losing it inside the bag. The surgeon pulls the grasped tissue little-by-little out of the patient making periodic circumferential cuts of any size so that more of the tissue can be pulled out until the entire piece of target tissue is removed. The result is a single elongated piece of removed target tissue instead of multiple small pieces. If not removed in one piece, the target tissue is removed in fewer pieces and in a more controlled manner. The bag 118 may be further retracted in between morcellations to bring the specimen closer to the surface. Once the tissue remaining in the bag 118 is small enough to easily fit through the incision, the bag 118 is completely removed.

The tissue guard described herein is typically employed with a containment bag. The bag is placed inside the body through a body opening. The body opening refers to any entranceway into the patient and may include and is not limited to incision sites and natural orifices. The target specimen is typically too large to be safely removed through the body opening and requires to be manipulated such as by cutting with a blade in order to extract the target specimen through the body opening. The body opening is generally smaller than the target specimen size. The target specimen is placed inside the bag and the mouth of the bag is pulled to the outside of the patient. The guard is placed inside the mouth of the bag and anchored across the body opening and the target specimen is pulled into the lumen of the guard. While in the lumen of the guard, the target specimen is in a protected morcellation zone wherein the surgeon may reach in with a blade to cut the target specimen for extraction. The guard protects against the stray blade and also provides a direct cutting surface against which tissue may be placed for reduction. The entire length of the guard typically defines the length of the morcellation zone protecting the bag and the tissue at the margins of the body opening. Additionally, a retractor may be employed. The retractor may be integrally formed with the bag or be a separate stand-alone device. A typical retractor described herein is a two-ringed retractor with a flexible sidewall material located between the two rings. The sidewall of the retractor is configured to be capable of being rolled about the first ring to retract the tissue at the margin of the body opening. If a retractor is employed it may be placed between the marginal tissue and the bag or inside the bag between the bag and the guard. The above description describes different variations of use of the guard, bag and retractor that is employed in manual morcellation. For power morcellation, the guard is inserted inside the bag and morcellation is carried out in a closed system. In another variation for power morcellation, a stability cap is connected to the proximal ring of the bag or to the proximal end of the guard and power morcellation is carried out. The stability cap serves to locate the vertical position of the blade ensuring that the blade does not extend beyond the predetermined morcellation zone inside the guard or at a short distance safely beyond the distal end of the guard. In another variation for power morcellation, a retractor is employed in which case the retractor is located between the marginal tissue and the bag or between the bag and the guard as previously described and power morcellation is carried out. In the previous variation, a stability cap may be employed in such a manner that it connects to the proximal ring of the retractor, the proximal ring of the bag, or to the proximal end of the guard and morcellation is carried out. In addition to the above variations, any one of the following approaches may be employed in conjunction with any of the variations above when performing a procedure such as a hysterectomy. In one variation, the bag is placed in through the vagina, the target specimen (e.g. uterus) is placed inside the bag while the bag is inside the body cavity, and then the mouth of the bag is pulled through an abdominal incision wherein the guard is inserted into the mouth of the bag, and morcellation, extraction and bag removal take place at the abdominal opening. In another variation, the bag is placed in through the vagina, the target specimen (e.g. uterus) is placed inside the bag while the bag is inside the body cavity, and then the mouth of the bag is pulled back through the vaginal canal wherein the guard is inserted into the mouth of the bag, and morcellation, extraction and bag removal take place at the vagina. In yet another variation, the bag is placed in through an abdominal incision, the target specimen (e.g. uterus) is placed inside the bag while the bag is inside the body cavity, and then the mouth of the bag is pulled through the vaginal canal wherein the guard is inserted into the mouth of the bag, and morcellation, extraction and bag removal take place at the vagina. In one other variation, the bag is placed in through an abdominal incision, the target specimen (e.g. uterus) is placed inside the bag while the bag is inside the body cavity, and then the mouth of the bag pulled back through the abdominal incision wherein the guard is inserted into the mouth of the bag, and morcellation, extraction and bag removal take place at the vagina. In another approach to morcellation of the uterus or other target specimen, the bag may be omitted. In such a case, an incision is made in the abdominal wall, the guard is placed across the incision in the abdominal, and the uterus or target specimen is detached and pulled through the central lumen of the guard with morcellation and extraction taking place at the abdominal incision. Alternatively, the target specimen (e.g. uterus) is approached through the vagina, the guard is placed inside the vaginal canal, and the target specimen is detached and pulled through the central lumen of the guard with morcellation and extraction taking place at the vagina. As a further variation of the abdominal approach with or without a bag, the procedure may be observed via a laparoscope inserted through the vagina. As a further variation of the vaginal approach with or without a bag, the procedure may be observed via a laparoscope inserted through an incision in the abdomen.

International PCT Application Serial No. PCT/US2015/27274 entitled "Systems and methods for tissue removal" filed on Apr. 23, 2015, is hereby incorporated herein by reference in its entirety.

It is understood that various modifications may be made to the embodiments disclosed herein. Therefore, the above description should not be construed as limiting, but merely as exemplifications of preferred embodiments. Those skilled in the art will envision other modifications within the scope and spirit of the present disclosure.

We claim:

1. A method for manufacturing a tissue guard to provide a pathway through a body opening, the method comprising the steps of:
   providing a mesh sleeve of material having a plurality of interwoven filaments defining interstices, the plurality of interwoven filaments being formed of a plastically deformable heat setting material; the mesh sleeve being substantially cylindrical in shape having a central lumen extending along a longitudinal axis between a proximal opening at a proximal end and a distal opening at a distal end;
   providing a mandrel having at least one outwardly flared flange;
   mounting the mesh sleeve onto the mandrel;
   annealing the mesh sleeve while the mesh sleeve is mounted onto the mandrel; and
   removing the mesh sleeve from the mandrel;
   the method further comprising the step of folding the mesh sleeve so as to create a double-layered sleeve of mesh material circumferentially enclosing the central lumen of the mesh sleeve; the folding step creating a fold at the distal end of the mesh sleeve with a first end and a second end of the mesh sleeve being adjacent to each other at the proximal end of the mesh sleeve, wherein the folding step is carried out prior to the step of mounting the mesh sleeve onto the mandrel.

2. The method of claim 1 wherein the plurality of interwoven filaments are made of thermosetting polymer filaments having a glass transition temperature; wherein the annealing step is performed at the glass transition temperature of the thermosetting polymer filaments.

3. The method of claim 1 wherein the annealing step further comprises the step of plastically deforming the plurality of interwoven filaments such that the mesh sleeve is molded and heat set so as to substantially conform to a shape of the mandrel when the mesh sleeve is removed from the mandrel.

4. The method of claim 1 wherein the plastically deformable heat setting material of the interwoven filaments provides the mesh sleeve with memory retention such that when the mesh sleeve is deformed and subsequently released it springs back to its original, undeformed shape.

5. The method of claim 1 wherein the mesh sleeve is mounted onto the mandrel such that the mandrel is located inside the central lumen and the mesh sleeve encompasses the mandrel.

6. The method of claim 1 further comprising the step of providing a ring adhered to the proximal end of the mesh sleeve after removing the mesh sleeve from the mandrel; the ring encompassing the proximal end of the mesh sleeve so as to cover the first and second ends of the plurality of interwoven filaments at the proximal end of the mesh sleeve; wherein the ring is formed by injection molding, extrusion molding or is molded over the proximal end of the mesh sleeve.

7. The method of claim 1 further comprising the step of heat sealing the proximal end of the mesh sleeve after removing the mesh sleeve from the mandrel; the heat sealing being performed using a hot tool for sealing the first and second ends of the plurality of interwoven filaments at the proximal end of the mesh sleeve.

8. The method of claim 1 further comprising the step of laying a bead of sealant or caulking along the proximal end of the mesh sleeve after removing the mesh sleeve from the mandrel; the bead encompassing the proximal end of the mesh sleeve so as to cover the first and second ends of the plurality of interwoven filaments at the proximal end of the mesh sleeve.

9. The method of claim 1 further comprising the step of providing a pull-wire at the distal end of the mesh sleeve to reduce a lateral dimension of the distal end of the mesh sleeve when the pull-wire is pulled and to return to an expanded relaxed configuration when the pull-wire is released, wherein the step of providing a pull-wire comprises the step of weaving the pull-wire circumferentially around the distal end of the mesh sleeve.

10. The method of claim 1 wherein the step of providing a mandrel comprises providing a mandrel having a first part removably interconnected to a second part; the first part having a first outwardly flared flange and the second part having a second outwardly flared flange; the mandrel further comprising a neck portion interconnecting the first and second outwardly flared flanges.

11. The method of claim 10 wherein the first and second outwardly flared flanges form respectively a first angle and a second angle with respect to a plane normal to the longitudinal axis; the first angle being 45 degrees and the second angle ranging from 0 to 45 degrees.

12. The method of claim 11 wherein the mesh sleeve is mounted onto the mandrel such that the proximal end of the mesh sleeve encompasses the first part of the mandrel forming a proximal flared flange angled circumferentially at the first angle and the distal end of mesh sleeve encompasses the second part of the mandrel forming a distal flared flange angled circumferentially at the second angle.

13. The method of claim 10 wherein the step of mounting the mesh sleeve onto the mandrel further comprises the steps of:

disconnecting the first and second parts of the mandrel;
the disconnecting step is performed by unscrewing the first part of the mandrel from the second part of the mandrel; and
reconnecting the first and second parts of the mandrel after mounting the mesh sleeve onto the mandrel.

14. The method of claim 1 further comprising the step of coating the proximal end of the mesh sleeve with a dispersion material; the dispersion material being made of silicone and/or urethane; wherein the coating step is performed after removing the mesh sleeve form the mandrel.

15. The method of claim 14 wherein the coating step comprises the step of dipping the proximal end of the mesh sleeve into the dispersion material or placing the proximal end of the mesh sleeve into a casting dish and pouring the dispersion material into the casting dish.

16. The method of claim 14 wherein the coating step further comprises the step of coating the proximal end of the mesh sleeve with an antimicrobial material.

\* \* \* \* \*